US009972088B2

(12) United States Patent
Fujiwara et al.

(10) Patent No.: US 9,972,088 B2
(45) Date of Patent: May 15, 2018

(54) IMAGE PROCESSING APPARATUS AND STORAGE MEDIUM

(71) Applicant: Konica Minolta, Inc., Tokyo (JP)

(72) Inventors: Koichi Fujiwara, Osaka (JP); Osamu Toyama, Kakogawa (JP); Hiroshi Yamato, Amagasaki (JP); Kenta Shimamura, Takatsuki (JP); Shintaro Muraoka, Hachioji (JP); Sho Noji, Tachikawa (JP)

(73) Assignee: KONICA MINOLTA, INC., Tokyo (JP)

(*) Notice: Subject to any disclaimer, the term of this patent is extended or adjusted under 35 U.S.C. 154(b) by 64 days.

(21) Appl. No.: 14/894,224

(22) PCT Filed: May 2, 2014

(86) PCT No.: PCT/JP2014/062131
§ 371 (c)(1),
(2) Date: Nov. 25, 2015

(87) PCT Pub. No.: WO2014/192505
PCT Pub. Date: Dec. 4, 2014

(65) Prior Publication Data
US 2016/0104283 A1 Apr. 14, 2016

(30) Foreign Application Priority Data

May 28, 2013 (JP) .................. 2013-112055

(51) Int. Cl.
G06K 9/00 (2006.01)
G06T 7/00 (2017.01)
(Continued)

(52) U.S. Cl.
CPC .......... G06T 7/0016 (2013.01); A61B 6/5217 (2013.01); A61B 6/5264 (2013.01);
(Continued)

(58) Field of Classification Search
CPC .................. G06Q 30/0241; G06T 2207/20076
See application file for complete search history.

(56) References Cited

U.S. PATENT DOCUMENTS 8,866,845 B2 * 10/2014 Leung .................. G06K 9/6892
345/633
9,198,628 B2 12/2015 Shimada et al.
(Continued)

FOREIGN PATENT DOCUMENTS

CN 102793551 A 11/2012
JP 06142100 A 5/1994
(Continued)

OTHER PUBLICATIONS

International Search Report; International Application No. PCT/JP2014/062131; Date of actual completion of the international search: Aug. 5, 2014; total of 1 page.
(Continued)

Primary Examiner — Oneal R Mistry
(74) Attorney, Agent, or Firm — Lucas & Mercanti, LLP

(57) ABSTRACT

An image processing apparatus of the present invention includes an image analysis unit that performs image analysis processing on a plurality of frame images constituting a base dynamic image to obtain an overall analysis value, a statistical analysis unit that performs statistical analysis processing on a diagnostic region using the overall analysis value to obtain a first analysis value, a reference statistical value generating unit that outputs a reference statistical value, and a display unit that displays the first analysis value and the reference statistical value together.

18 Claims, 13 Drawing Sheets

(51) Int. Cl.
*G06T 11/20* (2006.01)
*A61B 6/00* (2006.01)

(52) U.S. Cl.
CPC ............ *G06T 11/206* (2013.01); *A61B 6/486* (2013.01); *G06T 2207/10016* (2013.01); *G06T 2207/10124* (2013.01); *G06T 2207/20076* (2013.01); *G06T 2207/30061* (2013.01); *G06T 2210/41* (2013.01)

(56) References Cited

U.S. PATENT DOCUMENTS

| | | | |
|---|---|---|---|
| 2005/0053196 A1* | 3/2005 | Mostafavi | A61B 6/4441 378/98.12 |
| 2012/0078083 A1* | 3/2012 | McConnell | A61B 5/055 600/413 |
| 2012/0245453 A1* | 9/2012 | Tryggestad | A61B 6/463 600/413 |
| 2012/0300904 A1 | 11/2012 | Shimada | |
| 2015/0005659 A1* | 1/2015 | Masumoto | A61B 6/032 600/538 |

FOREIGN PATENT DOCUMENTS

| | | |
|---|---|---|
| JP | 2004312434 A | 4/2004 |
| JP | 2011083619 A | 4/2011 |

OTHER PUBLICATIONS

Written Opinion of the International Search Authority in Japanese; total of 4 pages, and English translation; total of 5 pages: International application No. PCT/JP2014/062131; International filing date: Feb. 5, 2014: Applicant: Konica Minolta, Inc.; Total of 9 pages.

Hiroki Kawashima, "Reproducibility of Dynamic Chest Radiography with a Flat-panel Detector: Respiratory Changes in Pixel Value", Japanese Journal of Radiological Technology, Jul. 14, 2009 (Jul. 14, 2009), vol. 65, No. 6, pp. 738 to 744; total of 7 pages.

Office Action dated Oct. 11, 2017 from corresponding Chinese Patent Application No. CN 201480030700.3 and English translation.

* cited by examiner

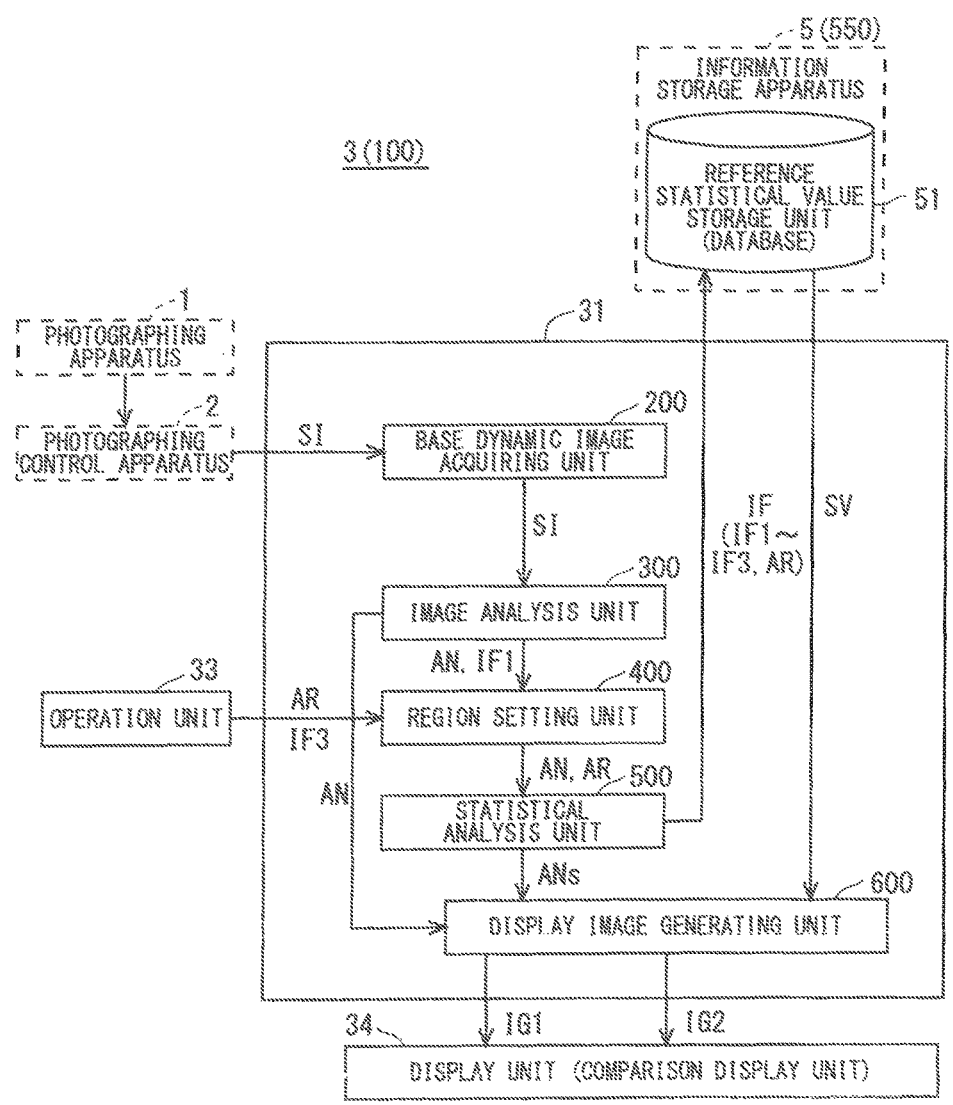
F I G . 2

IMAGE PROCESSING APPARATUS AND STORAGE MEDIUM

CROSS REFERENCE TO RELATED APPLICATION

This Application is a 371 of PCT/JP2014/062131 filed on May 2, 2014 which, in turn, claimed the priority of Japanese Patent Application No. JP2013-112055 filed on May 28, 2013, both applications are incorporated herein by reference.

TECHNICAL FIELD

The present invention relates to image processing technology for processing a dynamic image obtained by photographing a human body or an animal body.

BACKGROUND ART

In medical settings, an affected part in internal organs, skeletons, and the like is photographed, for example, with X-rays for various tests and diagnoses. Through application of recent digital technology, a dynamic image (an image group composed of a plurality of frame images) in which movement of an affected part is captured, for example, with X-rays can be acquired relatively easily.

In the recent digital technology, a dynamic image of a subject region including a diagnosis target region can be photographed with use of a semiconductor image sensor such as a flat panel detector (FPD), and thus an attempt to perform pathological analysis and diagnosis based on motion analysis of the diagnosis target region and the like, which cannot be performed in still image photography and diagnosis by conventional X-ray photography, is made. For example, in dynamic analysis of the chest with X-rays, the use of a luminance change in a lung field at each position in the lung field is considered to understand a functional state of the target region and to thereby support (CAD for X-ray dynamic images) diagnosis/treatment of a user such as a doctor.

For example, Patent Document 1 discloses an image processing apparatus that displays a plurality of diagnostic images side by side, and synchronizes operation between the diagnostic images to facilitate comparison therebetween.

Patent Document 2 discloses technology for generating, when each body part of a fetus is measured in an obstetric and gynecological hospital to determine the growth of the fetus and the presence or absence of any abnormality, a statistical value to be used as a standard, and displaying the statistical value and the measured value along with an ultrasonic image.

PRIOR ART DOCUMENTS

Patent Documents

Patent Document 1: Japanese Patent Application Laid-Open Publication No. 2011-83619
Patent Document 2: Japanese Patent Application Laid-Open Publication No. 6-142100

SUMMARY OF INVENTION

Problems to be Solved by Invention

In the above-mentioned technology disclosed in Patent Document 1, however, only comparison between current and past states of a diagnosis target person can be made, and comparison with a person other than the diagnosis target person, e.g., comparison considering a degree of variation among healthy individuals, cannot be made.

On the other hand, in the above-mentioned technology disclosed in Patent Document 2, comparison with a person other than the diagnosis target person can be made through use of the statistical value, but the ultrasonic image has been photographed as a still image, and thus comparison between an analysis value obtained based on frame images constituting a dynamic image and a statistical value corresponding to the analysis value cannot be made.

The present invention has been conceived in view of the above-mentioned matters, and aims to provide image processing technology enabling visual understanding of a difference between an analysis value obtained from a dynamic image of a body as a target for diagnosis and a statistical value calculated from a plurality of bodies different from the body as the target for diagnosis.

Means for Solving the Problems

In order to solve the above-mentioned problems, an image processing apparatus according to a first aspect of the present invention includes: a base dynamic image acquiring unit for acquiring a base dynamic image obtained by sequentially photographing, in a time direction, a state of a dynamic period in which a physical state of a target region in a body of a target object changes periodically, the target object being a human or an animal; an image analysis unit for performing image analysis processing on a plurality of frame images constituting the base dynamic image to obtain an overall analysis value in the target region as a whole; a statistical analysis unit for performing statistical analysis processing on a diagnostic region using the overall analysis value to obtain a first analysis value representing the diagnostic region, the diagnostic region being a whole or part of the target region; a reference statistical value generating unit for outputting, based on generation instruction information, a reference statistical value calculated using reference dynamic images of a plurality of past target objects; and a display unit for displaying the first analysis value and the reference statistical value to be compared with the first analysis value together.

The invention of a second aspect is the image processing apparatus according to the first aspect further including a region setting unit for performing region setting processing to set the diagnostic region from the target region, and the statistical analysis unit selectively performs the statistical analysis processing using part of the overall analysis value in the diagnostic region set in the region setting processing to obtain the first analysis value.

The invention of a third aspect is the image processing apparatus according to the first or second aspect, and the display unit further performs processing to display an overall analysis image based on the overall analysis value, and the overall analysis image includes an analysis still image configured as a still image based on the plurality of frame images.

The invention of a fourth aspect is the image processing apparatus according to the first or second aspect, and the display unit further performs processing to display an overall analysis image based on the overall analysis value, and the overall analysis image includes an analysis dynamic image configured as a dynamic image based on the plurality of frame images.

The invention of a fifth aspect is the image processing apparatus according to the fourth aspect, and the first analysis value includes a plurality of first analysis values calculated based on the plurality of frame images, and the display unit further performs processing to sequentially display the plurality of first analysis values in accordance with photographing time of the plurality of frame images to display the analysis dynamic image and the plurality of first analysis values in association with each other in terms of time.

The invention of a sixth aspect is the image processing apparatus according to the fifth aspect, and the display unit further performs processing to display a graph obtained by plotting the plurality of first analysis values in a direction of the photographing time, and the graph is associated with the analysis dynamic image in terms of time.

The invention of a seventh aspect is the image processing apparatus according to any one of the first to six aspects, and the reference statistical value includes a statistical value obtained after classification using, as a population parameter, at least one of: a photographing target parameter indicating information specific to the plurality of target objects; a disease information parameter indicating presence or absence of a disease and a state of the disease of the plurality of target objects; a photographing environment parameter indicating photographing environments in which the reference dynamic images have been photographed; and a respiratory state parameter indicating respiratory states of the target objects whose reference dynamic images have been photographed.

The invention of an eighth aspect is the image processing apparatus according to any one of the first to seventh aspects, and the image analysis processing includes processing to calculate at least one of: a luminance change value in corresponding pixels of the plurality of frame images; a distance indicating a size of the target region in each of the plurality of frame images; coordinates of a particular position in the target region in each of the plurality of frame images; an area of the target region in each of the plurality of frame images; and a moving amount of the particular position among the plurality of frame images.

The invention of a ninth aspect is the image processing apparatus according to any one of the first to eighth aspects, and the reference statistical value includes at least one of an average value, a maximum value, a minimum value, a range between the maximum value and the minimum value, and a degree of variation of a plurality of second analysis values obtained by performing processing similar to the image analysis processing and the statistical analysis processing on the reference dynamic images of the plurality of past target objects.

The invention of a tenth aspect is the image processing apparatus according to any one of the first to ninth aspects, and the target region includes a lung field region.

The invention of an eleventh aspect is the image processing apparatus according to any one of the first to tenth aspect, and the generation instruction information is at least one of a diagnostic region, image analysis information, statistical analysis information, and parameter information.

The invention of an twelfth aspect is a computer-readable non-transitory storage medium storing a program executed by a computer included in an image processing apparatus according to any one of the first to eleventh aspects.

Effects of Invention

According to the image processing apparatus according to the first to eleventh aspects, the statistical analysis processing is performed using the overall analysis value obtained by performing the image analysis processing on the plurality of frame images constituting the base dynamic image to obtain the first analysis value, and the first analysis value and the reference statistical value to be compared with the first analysis value are displayed together. That is to say, the first analysis value of the body of the target object as a current target for diagnosis and the reference statistical value calculated using the reference dynamic images of the plurality of past test objects other than the target object as the current target for diagnosis can be displayed simultaneously. As a result, a difference from the reference statistical value calculated from the plurality of past target objects can be understood at a glance, and thus diagnosis support information for a user such as a doctor can be provided. Consequently, time required for diagnosis can be reduced, and diagnosis of dynamics can be made properly and efficiently.

According to the invention of the second aspect, the region setting processing to set the diagnostic region from the target region is performed. This allows the user to set a desired region (e.g., a region with any abnormality) as the diagnostic region.

The statistical analysis unit selectively performs the statistical analysis processing using part of the overall analysis value in the diagnostic region set in the region setting processing to obtain the first analysis value. That is to say, the first analysis value in the diagnostic region and the reference statistical value in the diagnostic region can be obtained. For example, in a case where there is any abnormality only in a region of the target region on which the image analysis processing has been performed, the region with the abnormality can be set as the diagnostic region to obtain the first analysis value that is effective in diagnosis and to obtain the reference statistical value that is specific to the region with the abnormality. That is to say, since the first analysis value and the reference statistical value vary depending on a set region, information that is proper and significant in diagnosis can be obtained by narrowing down the diagnostic region.

According to the invention of the third aspect, the display unit further performs processing to display the overall analysis image based on the overall analysis value, and the overall analysis image includes the analysis still image configured as the still image based on the plurality of frame images. This allows the user to set a desired region (e.g., a region with any abnormality) as the diagnostic region while viewing the analysis still image.

If the analysis still image and the diagnostic image are viewed simultaneously, the first analysis value and the reference statistical value can be compared with each other, and an abnormality and the like can be identified also on the analysis still image.

According to the invention of the fourth aspect, the display unit further performs processing to display the overall analysis image based on the overall analysis value, and the overall analysis image includes the analysis dynamic image configured as the dynamic image based on the plurality of frame images. This allows the user to set a desired region (e.g., a region with any abnormality) as the diagnostic region while viewing the analysis dynamic image.

If the analysis dynamic image and the diagnostic image are viewed simultaneously, the plurality of first analysis values and the reference statistical value can be compared with each other, and an abnormality and the like can be identified also on the analysis dynamic image.

According to the invention of the fifth aspect, the display unit further performs processing to sequentially display the plurality of first analysis values in accordance with the photographing time of the plurality of frame images to display the analysis dynamic image and the plurality of first analysis values in association with each other in terms of time. That is to say, display of the first analysis value can be changed in synchronization with the change of the analysis dynamic image over time. As a result, diagnosis on a time period in which an abnormality occurs, a time period in which the abnormality disappears (returns to normal), and the like can be made in consideration of a time axis.

As a result, a change of a two-dimensional space on the frame images over time can visually be captured while it is compared with the reference statistical value.

According to the invention of the sixth aspect, the display unit further performs processing to display the graph obtained by plotting the plurality of first analysis values in the direction of the photographing time, and the graph is associated with the analysis dynamic image in terms of time. For example, if the graph is displayed so that a frame image of the analysis dynamic image currently being displayed can be known, the position (time) on the graph to which the frame image currently being displayed corresponds can be understood at a glance in synchronization with the change of display of the analysis dynamic image and the first analysis value over time. As a result, time at which any abnormality occurs can be identified on the graph.

According to the invention of the seventh aspect, the reference statistical value includes the statistical value obtained after classification using, as the population parameter, at least one of the photographing target parameter, the disease information parameter, the photographing environment parameter, and the respiratory state parameter. That is to say, a proper reference statistical value can be selected for display depending on the purpose of diagnosis from a plurality of patterns of statistical values calculated by changing the population parameter among the above-mentioned four parameters or combinations of any of the above-mentioned four parameters. Alternatively, the reference statistical value can be calculated for display depending on the purpose of diagnosis by changing the population parameter among the above-mentioned four parameters or combinations of any of the above-mentioned four parameters. For example, in a case where the target object as a target for diagnosis is a healthy individual, a statistical value calculated by using, as the population parameter, a plurality of healthy individuals as the plurality of target objects is used as the reference statistical value, whereas, in a case where the target object as the target for diagnosis is a patient with a particular disease, a statistical value calculated by using, as the population parameter, a plurality of patients with the particular disease as the plurality of target objects can be used as the reference statistical value. As described above, the population parameter used to calculate the reference statistical value can be changed depending on the purpose of diagnosis.

According to the invention of the eighth aspect, the image analysis processing includes processing to calculate at least one of the luminance change value, the distance indicating the size of the target region, the coordinates of the particular position, the area of the target region, and the moving amount of the particular position. As a result, the first analysis value that varies depending on diagnosis can be calculated, and the target region can comprehensively be diagnosed from various perspectives by calculating a plurality of types of first analysis values. As described above, the diagnosis support information that is effective to the user can be provided.

According to the invention of the ninth aspect, the reference statistical value is at least one of the average value, the maximum value, the minimum value, the range between the maximum value and the minimum value, and the degree of variation of the plurality of second analysis values obtained by performing processing similar to the image analysis processing and the statistical analysis processing on the reference dynamic images of the plurality of past target objects, and thus judgement on whether the target region is normal or not can efficiently be made when the reference statistical value is compared with the first value. As a result, the diagnosis support information that is effective to the user can be provided.

According to the invention of the tenth aspect, the target region is the lung field region, and thus diagnosis of dynamics on whether the lung field region is abnormal or not can be made while comparison with the reference statistical value is made. As a result, an abnormal region of the lung field region can efficiently be determined, time required for diagnosis of dynamics can be reduced, and diagnosis of dynamics can be made properly and efficiently.

According to the invention of the eleventh asepct, the reference statistical value that meets at least one of conditions of the diagnostic region, the image analysis information, the statistical analysis information, and the parameter information of the generation instruction information can be obtained.

According to the invention of the twelfth aspect, effects that are the same as those obtained in the invention of the first to eleventh aspects can be obtained.

The objects, features, aspects and advantages of the present invention will become more apparent from the following detailed description and the accompanying drawings.

BRIEF DESCRIPTION OF DRAWINGS

FIG. 2 is a block diagram showing a functional configuration of an image processing apparatus 3 according to Embodiment 1.

DESCRIPTION OF EMBODIMENTS

<1. Embodiment 1>

A radiographic dynamic image photographing system according to Embodiment 1 of the present invention is described below.

<1-1. Overall Configuration of Radiographic Dynamic Image Photographing System>

The radiographic dynamic image photographing system according to Embodiment 1 photographs a radiographic image of a human body or an animal body as a subject in a situation in which a physical state of a target region of the subject changes periodically over time.

Figure 1:
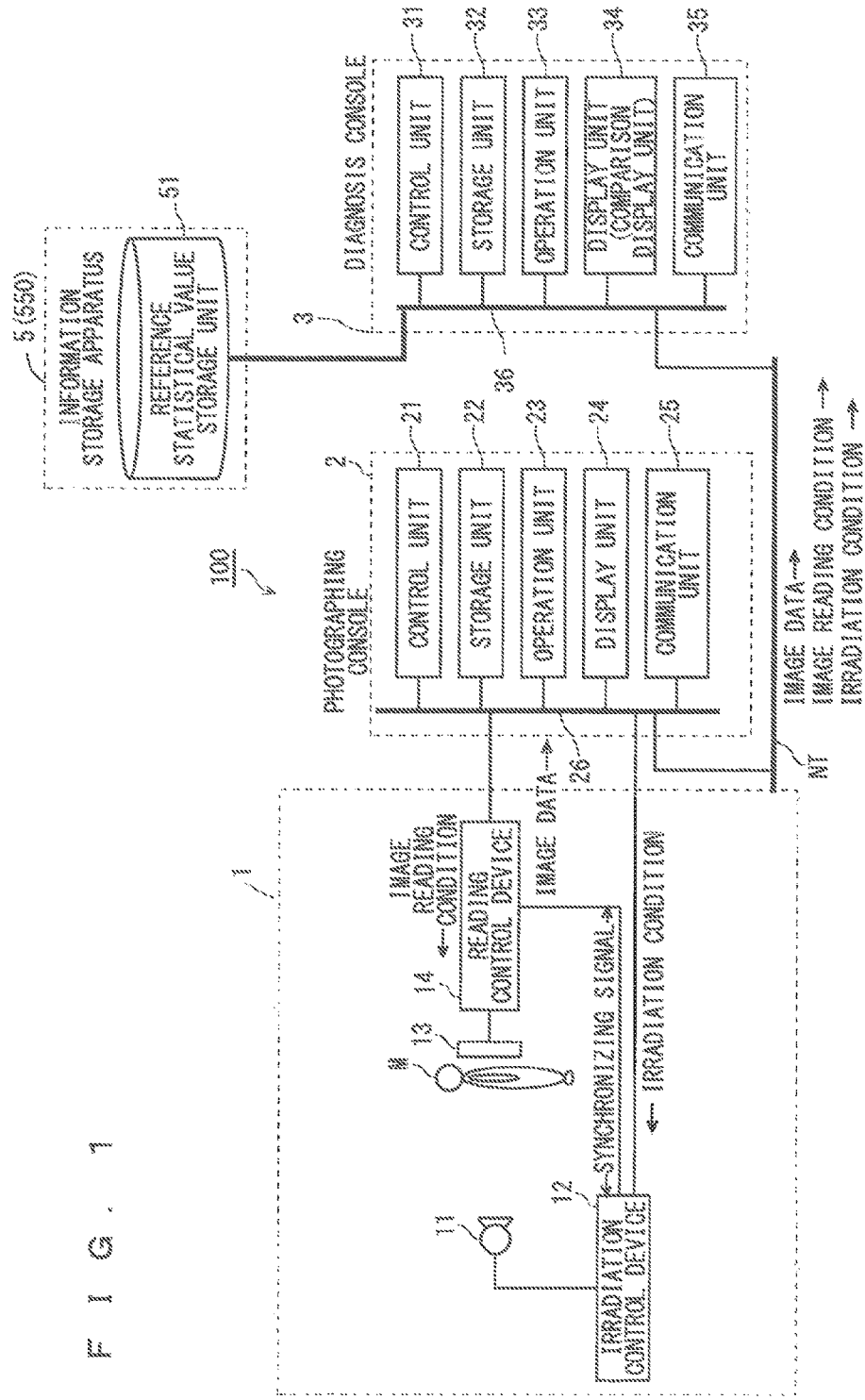
FIG. 1 is a diagram showing an overall configuration of a radiographic dynamic image photographing system 100 according to Embodiment 1.

FIG. 1 is a diagram showing an overall configuration of the radiographic dynamic image photographing system according to Embodiment 1. As shown in FIG. 1, a radiographic dynamic image photographing system 100 includes a photographing apparatus 1, a photographing control apparatus 2 (photographing console), and an image processing apparatus 3 (diagnosis console). The photographing apparatus 1 and the photographing control apparatus 2 are connected to each other by a communication cable or the like, and the photographing control apparatus 2 and the image processing apparatus 3 are connected to each other through a communication network NT such as a local area network (LAN). These apparatuses constituting the radiographic dynamic image photographing system 100 comply with the digital image and communications in medicine (DICOM) standard, and communicate with each other in accordance with the DICOM standard.

<1-1-1. Configuration of Photographing Apparatus 1>

The photographing apparatus 1 is configured, for example, by an X-ray photographing apparatus or the like, and photographs dynamics of the chest of a subject M involved in respiration. The dynamics are photographed by sequentially acquiring a plurality of images over time while repeatedly irradiating the chest of the subject M with radiation such as X-rays. A series of images acquired through the continuous photographing is referred to as a dynamic image. The images constituting the dynamic image are each referred to as a frame image.

As shown in FIG. 1, the photographing apparatus 1 includes an irradiation unit (a radiation source) 11, an irradiation control device 12, an imaging unit (a radiation detecting unit) 13, and a reading control device 14.

The irradiation unit 11 irradiates the subject M with radiation (X-rays) under control of the irradiation control device 12. Illustrated as an example is a system for a human body, and the subject M corresponds to a test target. The subject M is hereinafter also referred to as a "test subject".

The irradiation control device 12 is connected to the photographing control apparatus 2, and controls the irradiation unit 11 based on an irradiation condition input from the photographing control apparatus 2 for radiography.

The imaging unit 13 is configured by a semiconductor image sensor such as an FPD, and converts radiation having been emitted from the irradiation unit 11 and having passed through the test subject M into an electrical signal (image information).

The reading control device 14 is connected to the photographing control apparatus 2. The reading control device 14 controls switching units of pixels of the imaging unit 13 based on an image reading condition input from the photographing control apparatus 2 to switch reading of the electrical signals stored in the pixels, and reads the electrical signals stored in the imaging unit 13 to acquire image data. The reading control device 14 then outputs the acquired image data (frame images) to the photographing control apparatus 2. The image reading condition includes, for example, a frame rate, a frame interval, a pixel size, and an image size (a matrix size). The frame rate is the number of frame images acquired per second, and matches a pulse rate. The frame interval is a time from the start of an operation to acquire one frame image to the start of an operation to acquire the next frame image in continuous photography, and matches a pulse interval.

The irradiation control device 12 and the reading control device 14 are herein connected to each other, and exchange synchronizing signals with each other to synchronize an irradiation operation and an image reading operation with each other.

<1-1-2. Configuration of Photographing Control Apparatus 2>

The photographing control apparatus 2 outputs the irradiation condition and the image reading condition to the photographing apparatus 1 to control radiography and a radiographic image reading operation performed by the photographing apparatus 1, and also displays a dynamic image acquired by the photographing apparatus 1 so that a radiographer can check positioning and whether the image is an image suitable for diagnosis or not.

As shown in FIG. 1, the photographing control apparatus 2 includes a control unit 21, a storage unit 22, an operation unit 23, a display unit 24, and a communication unit 25, and these units are connected to one another by a bus 26.

The control unit 21 is configured by a central processing unit (CPU), a random access memory (RAM), and the like. The CPU of the control unit 21 reads a system program and various processing programs stored in the storage unit 22 in response to an operation of the operation unit 23 to develop them in the RAM, and performs various types of processing such as photographing control processing, which is described below, in accordance with the developed program to perform centralized control of an operation of each unit of the photographing control apparatus 2 and an operation of the photographing apparatus 1.

The storage unit 22 is configured by a nonvolatile semiconductor memory, a hard disk, and the like. The storage unit 22 stores various programs to be executed by the control unit 21 and parameters required for the programs to perform processing, or data on processing results, and the like.

The operation unit 23 includes a keyboard including cursor keys, numeric keys, and various function keys, and a pointing device such as a mouse, and outputs an instruction signal input through a key operation made on the keyboard, a mouse operation, or a touch panel to the control unit 21.

The display unit 24 is configured by a monitor such as a color liquid crystal display (LCD), and displays an input instruction from the operation unit 23, data, and the like in accordance with an instruction of a display signal input from the control unit 21.

The communication unit 25 includes a LAN adapter, a modem, a terminal adapter (TA), and the like, and controls data transmission and reception with each device connected to the communication network NT.

<1-1-3. Configuration of Image Processing Apparatus 3>

The image processing apparatus 3 acquires a dynamic image transmitted from the photographing apparatus 1 through the photographing control apparatus 2, and displays an image to be used by a doctor or the like to make diagnosis through reading.

As shown in FIG. 1, the image processing apparatus 3 includes a control unit 31, a storage unit 32, an operation unit 33, a display unit 34, and a communication unit 35, and these units are connected to one another by a bus 36.

The control unit 31 is configured by a CPU, a RAM, and the like. The CPU of the control unit 31 reads a system program and various processing programs stored in the storage unit 32 in response to an operation of the operation unit 33 to develop them in the RAM, and performs various types of processing in accordance with the developed program to perform centralized control of an operation of each unit of the image processing apparatus 3 (described in detail below).

The storage unit 32 is configured by a nonvolatile semiconductor memory, a hard disk, and the like. The storage unit 32 stores various programs to be executed by the control unit 31 and parameters required for the programs to perform processing, or data on processing results, and the like. For example, the storage unit 32 stores an image processing program for performing image processing, which is described below. These various programs are stored in the form of readable program codes, and the control unit 31 sequentially performs operations in accordance with the program codes.

The operation unit 33 includes a keyboard including cursor keys, numeric keys, and various function keys, and a pointing device such as a mouse, and outputs an instruction signal input through a key operation made on the keyboard, a mouse operation, or a touch panel to the control unit 31.

The display unit 34 is configured by a monitor such as a color LCD, and displays an input instruction from the operation unit 33, data, and a display image, which is described below, in accordance with an instruction of a display signal input from the control unit 31.

The communication unit 35 includes a LAN adapter, a modem, a TA, and the like, and controls data transmission and reception with each device connected to the communication network NT.

<1-2. Configuration of Information Storage Apparatus 5>

As shown in FIG. 1, an information storage apparatus 5 is configured, for example, by a database server including a personal computer or a workstation, includes a database (reference statistical value storage unit) 51, and performs data transmission and reception with the control unit 31 through the bus 36. A collection of reference statistical values considering possible photographing information and the like is stored in advance in the database 51 (described in detail below).

The image processing apparatus 3 in Embodiment 1 is described in detail below.

<1-3. Problem Arising When Diagnosis of Dynamics is Made>

A problem arising when diagnosis of dynamics is made is described as a premise of description of the details of the image processing apparatus 3 in the present embodiment.

In lung function diagnosis using X-ray dynamic images, when a user such as a doctor diagnoses the results of analysis performed based on a luminance change in the dynamic images, the opinion that "it is hard to know a luminance change indicating a normal lung function as it varies even among healthy individuals" is heard from the user. That is to say, only an analysis image of a patient as a target for diagnosis is displayed on a screen displayed in diagnosis of dynamics, and comparison with other people cannot be made.

To address the problem, the present invention aims to calculate a statistical value of analysis results in advance from X-ray dynamic images of a plurality of test subjects (e.g., a plurality of healthy individuals and patients with a particular disease) that suit a diagnostic application, and to display the statistical value along with analysis results of the test subject M as a target for diagnosis.

<1-4. Specific Configuration of Image Processing Apparatus 3>

The image processing apparatus 3 of the radiographic dynamic image photographing system 100 in Embodiment 1 of the present invention displays a difference between an analysis value of a body as a target for diagnosis and a statistical value calculated from a plurality of bodies different from the body as the target for diagnosis to reduce time required for diagnosis of dynamics.

A functional configuration achieved by the image processing apparatus 3 is described below.

<1-4-1. Functional Configuration of Image Processing Apparatus 3>

FIG. 2 shows a functional configuration achieved by the control unit 31 through operation of the CPU and the like in accordance with various programs in the image processing apparatus 3 of the radiographic dynamic image photographing system 100, along with other configurations. The image processing apparatus 3 in the present embodiment uses a dynamic image obtained by photographing the chest mainly including the heart and both lungs.

The control unit 31 is mainly composed of a base dynamic image acquiring unit 200, an image analysis unit 300, a region setting unit 400, a statistical analysis unit 500, and a display image generating unit 600. The control unit 31 performs data transmission and reception with a reference statistical value generating unit 550 (corresponding to the information storage apparatus 5 including the above-mentioned reference statistical value storage unit 51) through the bus 36.

Although the following description is made on the assumption that the functional configuration of the control unit 31 as shown in FIG. 2 is achieved through execution of a program installed in advance, the functional configuration may be achieved by a dedicated hardware configuration.

Details of processing performed by the base dynamic image acquiring unit 200, the image analysis unit 300, the region setting unit 400, the statistical analysis unit 500, the information storage apparatus 5, and the display image generating unit 600 are sequentially described with reference to FIG. 2.

<1-4-1-1. Base Dynamic Image Acquiring Unit 200>

The base dynamic image acquiring unit 200 acquires a base dynamic image composed of a plurality of frame images obtained by the reading control device 14 of the photographing apparatus 1 sequentially photographing, in a time direction, a state of a dynamic period in which a physical state of a target region in a body of the test subject M changes periodically. The target region in the present embodiment is a lung field region. That is to say, as shown in FIG. 2, the photographing control apparatus 2 is disposed between the photographing apparatus 1 and the image processing apparatus 3, and detected data (a plurality of frame images SI) stored in the storage unit of the photographing control apparatus 2 is output to the communication unit 35 of the image processing apparatus 3 through the communication unit 25.

Figure 3:
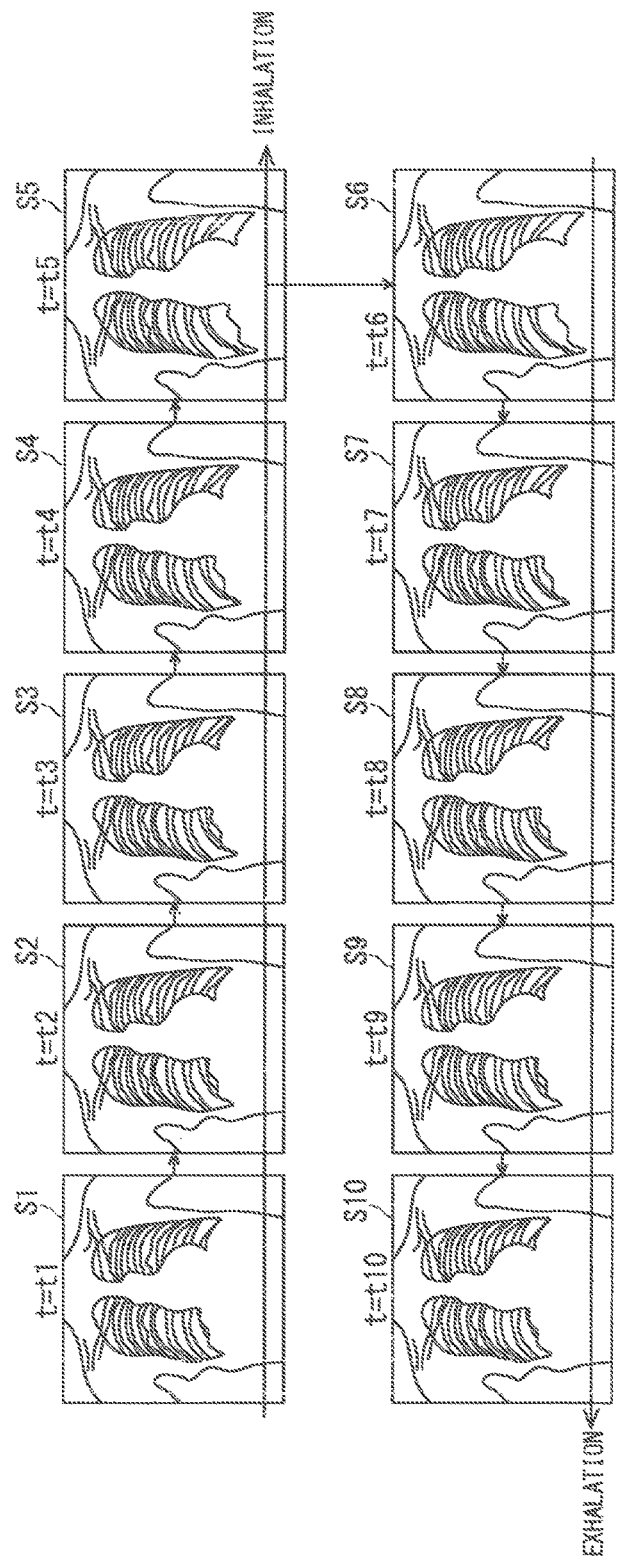
FIG. 3 is a diagram illustrating a dynamic image obtained through radiographic dynamic image photography.

FIG. 3 is a diagram illustrating a base dynamic image obtained, as for dynamics of the chest of the subject M involved in respiration, through radiographic dynamic image photography. As illustrated in FIG. 3, frame images S1 to S10 (SI) acquired by the base dynamic image acquiring unit 200 are images obtained by continuously photographing one period of the respiratory cycle at constant photographing timings. Specifically, images photographed at photographing timings indicated by time t=t1, t2, t3, . . . , and t10 correspond to the frame images S1, S2, S3, . . . , and S10, respectively.

<1-4-1-2. Image Analysis Unit 300>

The image analysis unit 300 performs image analysis processing on the plurality of frame images SI constituting the base dynamic image to obtain an overall analysis value AN in the lung field region as a whole. The image analysis processing herein refers to processing to calculate at least one of (i) a luminance change value in corresponding pixels of the plurality of frame images SI, (ii) the distance indicating a size of the lung field region in each of the plurality of frame images SI, (iii) coordinates of a particular position in the lung field region in each of the plurality of frame images SI, (iv) the area of the lung field region in each of the plurality of frame images SI, and (v) a moving amount of the particular position among the plurality of frame images SI. Note that (i) to (v) are hereinafter referred to as "image analysis information IF1".

Figure 4:
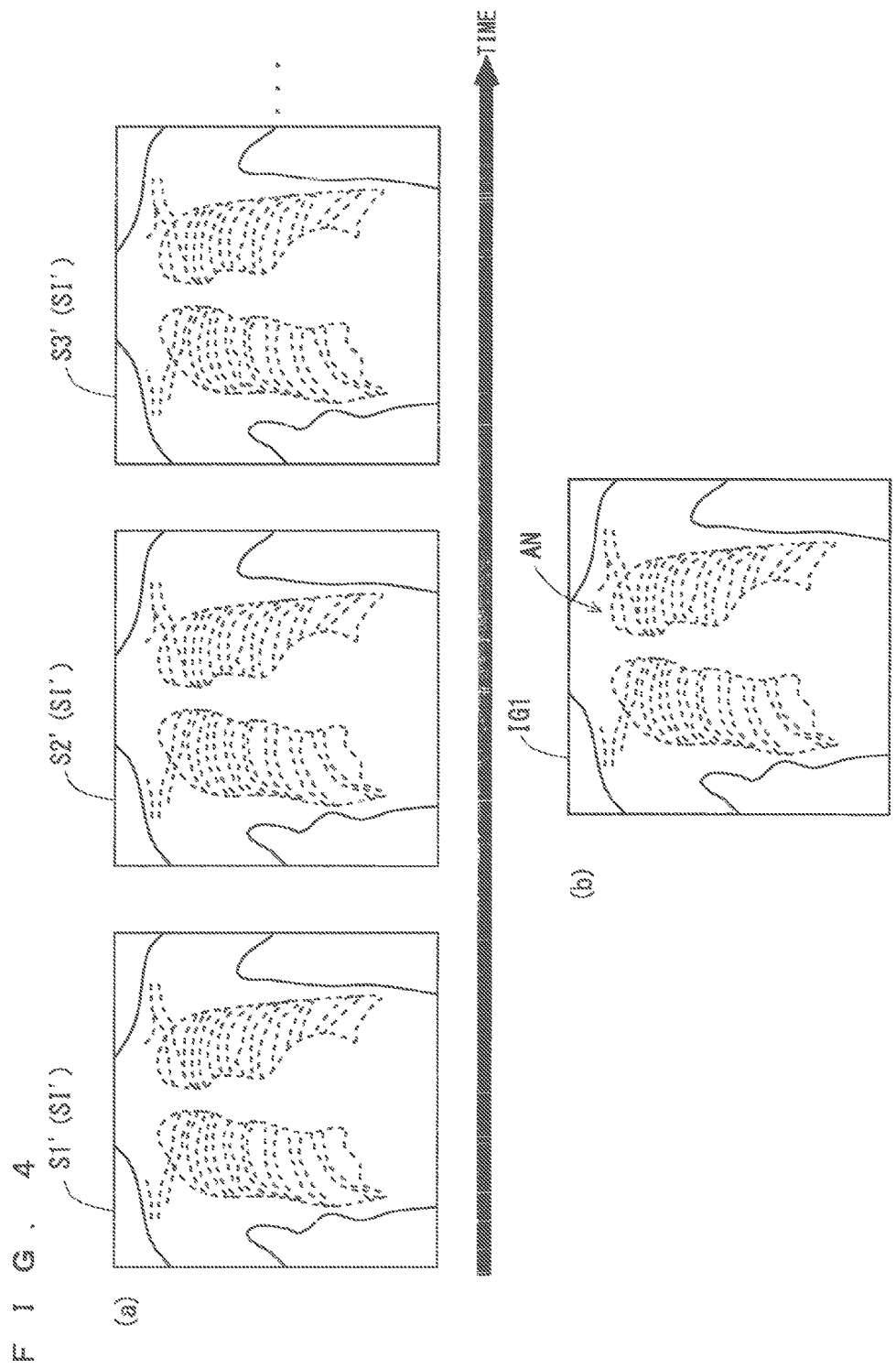
FIG. 4 is a schematic diagram for explaining image analysis processing.
Figure 5:
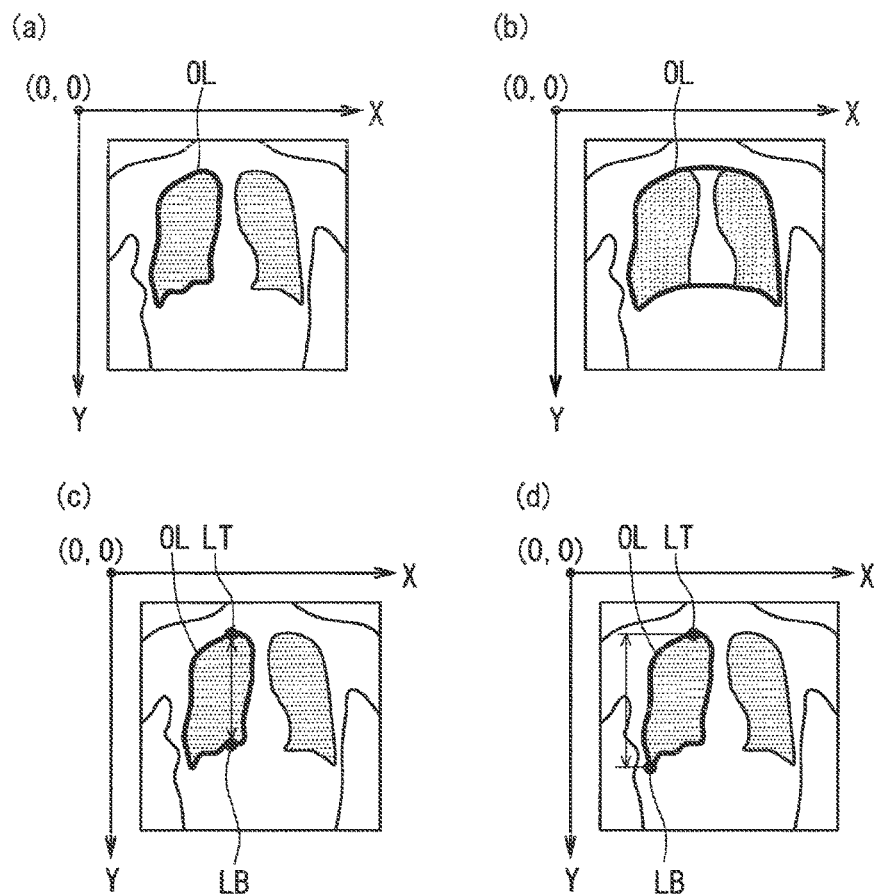
FIG. 5 is a schematic diagram for explaining the image analysis processing.

Cases where (i) the luminance change value, (ii) the size of the lung field region, and (iv) the area of the lung field region are calculated in the image analysis processing are described below as examples. FIGS. 4 and 5 are schematic diagrams for explaining the image analysis processing.

First, FIG. 4 illustrates a case where (i) the luminance change value is calculated in the image analysis processing to obtain the overall analysis value AN in the lung field region as a whole.

The left diagram of part (a) of FIG. 4 illustrates a difference image S1' (SI') showing a difference between corresponding pixels of the frame image S1 photographed at time t=t1 and the frame image S2 photographed at time t=t2 of FIG. 3, the middle diagram of part (a) of FIG. 4 illustrates a difference image S2' (SI') showing a difference between corresponding pixels of the frame image S2 photographed at time t=t2 and the frame image S3 photographed at time t=t3 of FIG. 3, and the right diagram of part (a) of FIG. 4 illustrates a difference image S3' (SI') showing a difference between corresponding pixels of the frame image S3 photographed at time t=t3 and the frame image S4 photographed at time t=t4 of FIG. 3. Although only three difference images SI' are described herein, similar difference processing is performed on all the frame images SI constituting the base dynamic image in the image analysis processing.

Although the difference images SI' are described for convenience's sake in the present embodiment, there is no need to actually generate these images, and only a difference value between frame images SI is necessary. The difference value corresponds to the luminance change value.

Part (b) of FIG. 4 illustrates an image obtained by extracting and plotting, for each pixel, a maximum luminance change value between corresponding pixels of the difference images SI', and corresponds to an overall analysis image (analysis still image) IG1 generated in display image generation processing described below (described in detail below). That is to say, the image analysis unit 300 performs processing to extract a maximum luminance change value between corresponding pixels calculated in the image analysis processing in the lung field region as a whole to obtain the overall analysis value AN, and outputs the overall analysis value AN to the display image generating unit 600, which is described below.

The overall analysis value AN is described in part (b) of FIG. 4 to be obtained by extracting a maximum luminance change value between corresponding pixels, but is not limited to this example, and may be any of a total luminance change value between corresponding pixels, an average luminance change value between corresponding pixels, a minimum luminance change value between corresponding pixels, and a median luminance change value between corresponding pixels, for example.

Next, parts (a) and (b) of FIG. 5 illustrate a case where (iv) the area of the lung field region is calculated in the image analysis processing. As illustrated in parts (a) and (b) of FIG. 5, a contour of a lung field portion can be extracted to define the number of pixels in a region enclosed by the contour as the area of the lung field portion. The lung field portion may be extracted for each of a left lung field portion and a right lung field portion as illustrated in part (a) of FIG. 5, or may be extracted as a contour including regions of the heart and the spine as illustrated in part (b) of FIG. 5. Conventional technology (see, for example, "Image feature analysis and computer-aided diagnosis: Accurate determination of ribcage boundary in chest radiographs", Xin-Wei Xu and Kunio Doi, Medical Physics, Volume 22(5), May 1995, pp. 617-626) may be used as the extraction method.

Parts (c) and (d) of FIG. 5 illustrate a case where (ii) the distance (distance between feature points of the lung field region) indicating the size of the lung field region is calculated in the image analysis processing. As illustrated in parts (c) and (d) of FIG. 5, the distance between feature points of the lung field region is calculated in each of the plurality of frame images SI in the image analysis processing. That is to say, the lung field portion is extracted in a method similar to the above-mentioned method (see parts (a) and (b) of FIG. 5, two feature points are obtained from the extracted region, and the distance between the two points is obtained to detect it as the distance indicating the size of the lung field region.

Parts (c) and (d) of FIG. 5 illustrate positions of the feature points of the lung field region in a case where the contour OL of the lung field portion of part (a) of FIG. 5 is used. In a case where a change in length (lung field length) from an upper end LT to a lower end LB of a lung region is calculated, part (c) of FIG. 5 illustrates an example in which extraction is performed with an apical portion of the lung being the upper end LT of the lung region and with an intersection of the diaphragm and a straight line extending downward from the apical portion of the lung in a body axis direction being the lower end LB of the lung region, and part (d) of FIG. 5 illustrates an example in which extraction is performed with the apical portion of the lung being the upper end LT of the lung region and with the costophrenic angle being the lower end LB of the lung region.

Figure 6:
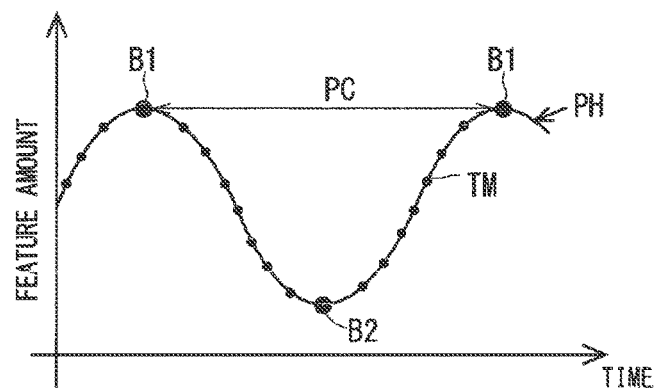
FIG. 6 is a schematic diagram showing a respiratory phase showing waveform data on a respiratory vibration value in time sequence along with photographing timing.

FIG. 6 is a schematic diagram of a respiratory phase PH showing, in time sequence, a feature amount, such as the area of the lung field region and the distance between feature points, calculated in the image analysis processing, and shows results of monitoring the feature amount in a time direction at each photographing timing TM. As shown in FIG. 6, one period PC of respiration (respiratory cycle) is composed of inhalation and exhalation, i.e., one exhalation and one inhalation. In inhalation, a region of the lung field in the thoracic cage becomes larger as the diaphragm descends for inhalation. A time of inhalation to a maximum extent (a switching point from inhalation to exhalation) is a maximum inhalation time B1. In exhalation, the region of the lung field becomes smaller as the diaphragm ascends for exhalation, and a time of exhalation to a maximum extent (a switching point from exhalation to inhalation) is a maximum exhalation time B2.

<1-4-1-3. Region Setting Unit 400>

The region setting unit 400 performs region setting processing to set a diagnostic region AR from the lung field region (see FIG. 2). As an example of the region setting processing, there is a method of setting the diagnostic region AR based on setting information input from the operation unit 33. That is to say, the setting information input from the operation unit 33 refers to setting information indicating a part of the lung field region as the diagnostic region AR, and is input by a user via the operation unit 33 while the user views the overall analysis image IG1, which is described below. Designation may be made by the user by any method such as rectangular designation, elliptical designation, and freehand designation.

As an example of the region setting processing other than designation made by the user, a region prepared in advance as a region obtained from information on the structure of the lung field and the like may be used as the diagnostic region AR to which attention is paid. Candidates for the diagnostic region AR include an "entire lung field", a "right or left lung field", "superior, middle, and inferior lobes (in the case of the right lung field)", "superior and inferior lobes (in the case of the left lung field)", "regions obtained by equally dividing the lung field in a direction of gravity", and "regions calculated by the distance from the hilum", for example, but these candidates are just examples, and are not limited to these examples.

The following description is made by taking cases where the diagnostic region AR to which attention is paid is the "superior, middle, and inferior lobes (in the case of the right lung field)", the "regions obtained by equally dividing the lung field in the direction of gravity", and the "regions calculated by the distance from the hilum" as examples.

Figure 7:
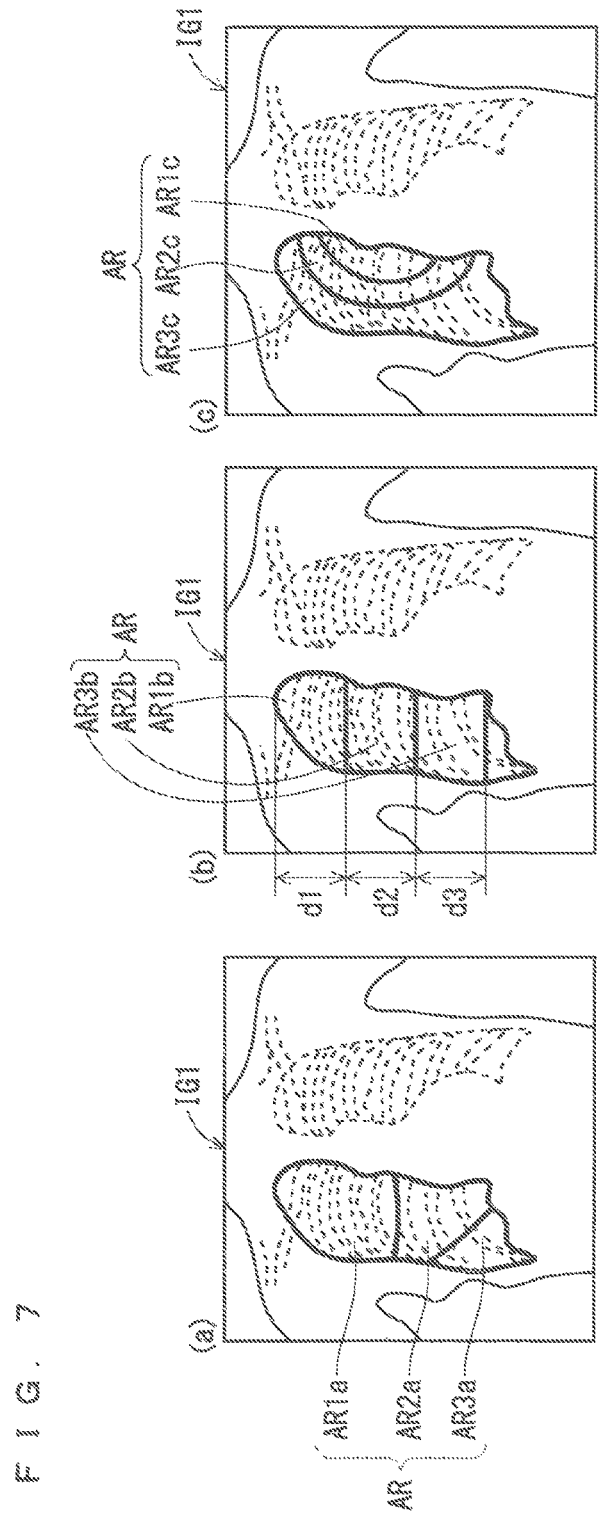
FIG. 7 is a schematic diagram for explaining region setting processing.

FIG. 7 is a schematic diagram for explaining the region setting processing, and part (a) of FIG. 7 is a schematic diagram for explaining a case where the candidates for the diagnostic region AR are the "superior, middle, and inferior lobes (in the case of the right lung field)", part (b) of FIG. 7 is a schematic diagram for explaining a case where the candidates for the diagnostic region AR are the "regions obtained by equally dividing the lung field in the direction of gravity", and part (c) of FIG. 7 is a schematic diagram for explaining a case where the candidates for the diagnostic region AR are the "regions calculated by the distance from the hilum".

Although the overall analysis image IG1 is shown in each of the parts (a) to (c) of FIG. 7 for convenience's sake, the display unit 34 does not display the overall analysis image IG1 in a case where the region prepared in advance is used in the region setting processing.

As illustrated in part (a) of FIG. 7, the right lung region in the overall analysis image IG1 can be classified into a superior lobe AR1a, a middle lobe AR2a, and an inferior lobe AR3a to set the diagnostic region AR. That is to say, a standard model of these lobes can be prepared, and modified for collation to set the diagnostic region AR.

As illustrated in part (b) of FIG. 7, the entire right lung region in the overall analysis image IG1 can be divided into three equal regions, namely a region AR1b, a region AR2b, and a region AR3b, in the direction of gravity for classification to set the diagnostic region. That is to say, the distance of the entire right lung region in the direction of gravity is defined as the distance from the apical portion of the lung to the diaphragm, and the diagnostic region is set so that distances d1, d2, and d3 are equal to one another (d1=d2=d3). The region is divided along the direction of gravity because the sizes of alveoli vary depending on gravity, and thus a luminance value varies among the regions AR1b to AR3b. Although the distance of the entire right lung region in the direction of gravity is herein defined as the distance from the apical portion of the lung to the diaphragm, the distance is not limited to this example, and may be defined as another distance.

As illustrated in part (c) of FIG. 7, the hilum of the right lung region in the overall analysis image IG1 can be detected first, and the distance from the hilum can be calculated to classify the right lung region into a region AR1c, a region AR2c, and a region AR3c in accordance with the calculated distance to thereby set the diagnostic region AR. As in part (a) of FIG. 7, for example, a standard model can be prepared, and modified for collation to detect the hilum. This setting method is effective mainly in the case of analyzing a blood flow.

In the region setting processing, a method of holding a diagnostic region set with respect to the test subject M in the past in the storage unit 32, and utilizing the diagnostic region AR again may be used in place of a method for setting the region through designation made by the user and a method for setting the region using the region prepared in advance as described above.

The diagnostic region AR is treated as a "region", but may be treated as a "point". In a case where the diagnostic region AR is a point, the point may be set as a point (e.g., a point located a certain distance below the apical portion of the lung and a point located a certain distance above the diaphragm) obtained from information on the structure of the lung field and the like, or may be designated by the user as in the case where the diagnostic region AR is a region.

<1-4-1-4. Statistical Analysis Unit 500>

The statistical analysis unit 500 performs statistical analysis processing on the diagnostic region AR that is a whole or part of the lung field region using the overall analysis value AN to obtain a first analysis value ANs representing the diagnostic region AR. In the present embodiment, the region setting unit 400 outputs the diagnostic region AR set in the region setting processing to the statistical analysis unit 500, and thus the statistical analysis unit 500 selectively performs the statistical analysis processing using part of the overall analysis value AN in the diagnostic region AR set in the region setting processing to obtain the first analysis value ANs (see FIG. 2).

The statistical analysis processing herein refers to processing to calculate any of an average value, a total value, a maximum value, a minimum value, a median value, and the like of the overall analysis value AN in the diagnostic region AR. The statistical analysis unit 500 thus obtains any of the average value, the total value, the maximum value, the minimum value, the median value, and the like (these values are hereinafter referred to as "statistical analysis information IF2") of the overall analysis value AN in the diagnostic region AR as the first analysis value ANs representing the diagnostic region AR.

As shown in FIG. 2, the statistical analysis unit 500 then outputs the diagnostic region AR, the image analysis information IF1, the statistical analysis information IF2, and parameter information IF3, which is described below, to the information storage apparatus 5 (see FIG. 2).

<1-4-1-5. Information Storage Apparatus 5>

The information storage apparatus 5 outputs a reference statistical value SV based on generation instruction information at least including diagnostic information. The generation instruction information IF refers collectively to the diagnostic region AR, the image analysis information IF1, the statistical analysis information IF2, and the parameter information IF3, which is described below.

The reference statistical value SV herein refers to a statistical value that is calculated based on a plurality of second analysis values obtained by performing image analysis processing and statistical analysis processing similar to the above-mentioned processing on reference dynamic images of a plurality of past test subjects, and is used mainly to judge whether the first analysis value ANs is good or bad. For example, in a case where the first analysis value ANs is an average luminance change value between corresponding pixels, the second analysis values are average luminance change values between corresponding pixels of the past test subjects. In a case where the first analysis value ANs is judged to be not good (bad) as a result of comparison with the reference statistical value SV, the extent to which the first analysis value ANs is away from values of healthy individuals can be known from the difference between the reference statistical value SV and the first analysis value ANs.

The reference statistical value SV refers to a statistical value that is at least one of an average value, a maximum value, a minimum value, a range between the maximum value and the minimum value, and a degree of variation (the standard deviation and variance) obtained using the second analysis values. The past "test subjects" in the reference dynamic images refer to the third parties other than the test subject M who is a current target for diagnosis.

When the generation instruction information IF (the diagnostic region AR, the image analysis information IF1, the statistical analysis information IF2, and the parameter information IF3, which is described below) is input from the statistical analysis unit 500 (see FIG. 2), the information storage apparatus 5 generates the reference statistical value SV that meets these conditions. This means that the reference statistical value SV can be switched depending on the conditions of the diagnostic region AR, the image analysis information IF1, the statistical analysis information IF2, and the parameter information IF3, which is described below.

The parameter information IF3 of the generation instruction information IF is described below. That is to say, the parameter information IF3 is information indicating classification using, as a population parameter, at least one of a "photographing target parameter IO" indicating information specific to a plurality of test subjects, a "disease information parameter IS" indicating the presence or absence of a disease and a state of the disease of the test subjects, a "photographing environment parameter IE" indicating photographing environments in which the reference dynamic images have been photographed, and a "respiratory state parameter IB" indicating respiratory states of the test subjects whose reference dynamic images have been photographed. Each of the parameters is further classified from the following perspectives.

That is to say, the "photographing target parameter IO" is classified into sex, age, a body type and a body thickness, and the like, the "disease information parameter IS" is classified into a healthy individual, a patient with a particular disease (e.g., a patient with COPD), severity of a disease, and the like, the "photographing environment parameter IE" is classified into tube voltage, tube current, photographing time, a radiation dose, a photographing distance, a photographing direction P-A (posteroanterior view) or A-P (anteroposterior view), a position during photography (a standing position and a lying position [a supine position, a side-lying position, and a prone position]), and the like, and the "respiratory state parameter IB" is classified into inhalation, exhalation, breath holding, and the like. The respiratory state, such as inhalation and exhalation, can be obtained herein from a dynamic image using a method as shown in FIG. 6 described above.

Candidates for the population parameter are not limited to the above-mentioned parameters IO, IS, IE, and IB, and may be other parameters. By combining these parameters, various patterns of population parameters can be used to generate the reference statistical value SV.

As described above, it is preferable to generate the reference statistical value SV by changing the population parameter in accordance with the diagnostic information. The parameter used to generate the reference statistical value SV can be designated by the statistical analysis unit 500 outputting the parameter information IF3 to the information storage apparatus 5 (see FIG. 2). That is to say, any of the above-mentioned parameters IO, IS, IE, and IB or a combination of any of the above-mentioned parameters IO, IS, IE, and IB is designated as the parameter information IF3. As a method for inputting the parameter information IF3, the user may directly designate the parameter information IF3 via the operation unit 33 as shown in FIG. 2, or the parameter information IF3 may automatically be output from the photographing control apparatus 2, for example.

<1-4-1-5-1. Reference Statistical Value Storage Unit (Database) 51>

The reference statistical value storage unit (database) 51 is described next. The database 51 stores therein the reference statistical values SV according to the present embodiment so that the reference statistical values SV can be grouped based on the diagnostic region AR, the image analysis information IF1, the statistical analysis information IF2, and the parameter information IF3, for example. That is to say, the database 51 stores therein a collection of the reference statistical values SV in accordance with an attribute indicated by the generation instruction information IF input from the statistical analysis unit 500, and can output the reference statistical value SV that matches the generation instruction information IF. That is to say, the collection of the reference statistical values SV is provided in advance with attribute information, and is stored in the database 51 for each group. The attribute information herein refers to information relating to sex, age, weight, height, a body type and a body thickness, and the like in the case of the photographing target parameter IO of the parameter information IF3, for example.

The following description on a conceptual configuration of the database 51 focuses on a conceptual configuration of the parameter information IF3 while information on the diagnostic region AR, the image analysis information IF1, and the statistical analysis information IF2 of the generation instruction information IF is fixed, but the diagnostic region AR, the image analysis information IF1, and the statistical analysis information IF2 have a similar conceptual configuration. The database 51 herein thus has a conceptual configuration in which the collection of the reference statistical values SV are grouped and stored based on the photographing target parameter IO, the disease information parameter IS, the photographing environment parameter IE, and the respiratory state parameter IB, for example.

Description is made using the most simplified example in a case where the photographing target parameter IO is "sex", the disease information parameter IS is a "healthy individual or non-healthy individual", the photographing environment parameter IE is a "photographing direction P-A (posteroanterior view) or A-P (anteroposterior view)", and the respiratory state parameter IB is "exhalation or inhalation".

Figure 8:
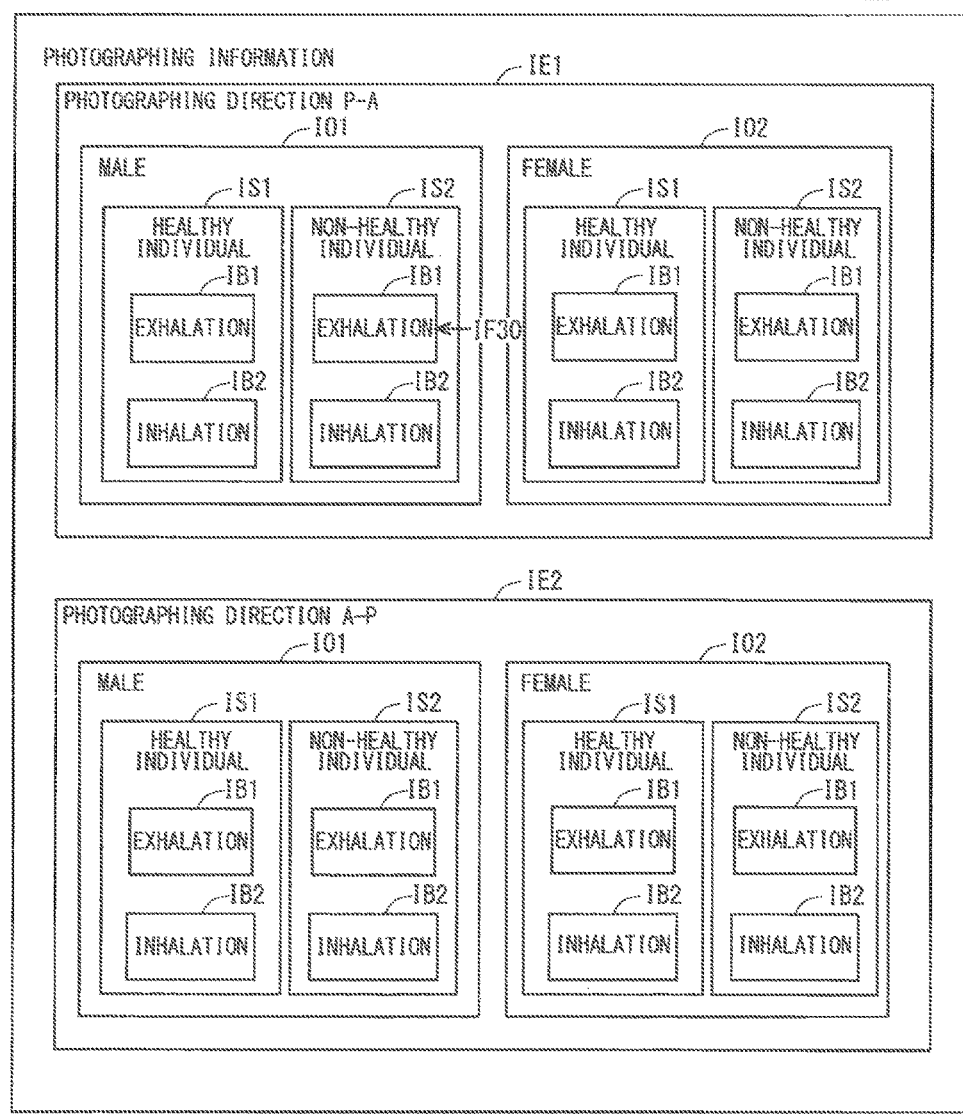
FIG. 8 is a conceptual diagram showing an example of a hierarchical reference statistical value in a database 51.

FIG. 8 is a conceptual diagram showing an example of hierarchical parameter information in the database 51. Description with use of FIG. 8 focuses on the hierarchy of the parameter information IF3 under the premise that, as the generation instruction information IF, the diagnostic region AR is the right lung field, the image analysis information IF1 is a luminance change value, and the statistical analysis information IF2 is an average value.

As shown in FIG. 8, the photographing environment parameter IE "photographing direction" is the highest concept of all the photographing target parameter IO "male IO1 or female IO2", the disease information parameter IS "healthy individual IS1 or non-healthy individual IS2", and the photographing environment parameter IE "posteroanterior view IE1 or anteroposterior view IE2", and thus the photographing environment parameter IE "photographing direction" is first broadly divided into parameter information IE1 "posteroanterior view" and parameter information IE2 "anteroposterior view", and the reference statistical values SV are grouped and stored (accumulated) therein. Next, the photographing target parameter IO "sex" is a higher concept than the disease information parameter IS "healthy individual or non-healthy individual", and thus the reference statistical values SV in the parameter information IO1 "male" and the parameter information IO2 "female" are stored in each of the parameter information IE1 and the parameter information IE2. The disease information parameter IS "healthy individual or non-healthy individual" is a higher concept than the respiratory state parameter IB "exhalation or inhalation", and thus the reference statistical values SV in the parameter information IS1 "healthy individual" and the parameter information IS2 "non-healthy individual" are stored in each of the parameter information IO1 and the parameter information IO2. Furthermore, the reference statistical values SV in the parameter information IB1 "exhalation" and the parameter information IB2 "inhalation" are stored in each of the parameter information IS1 and the parameter information IS2.

Therefore, the parameter information in a case where the parameter information IF3 is a combination of the photographing target parameter IO "male IO1", the disease information parameter IS "non-healthy individual IS2", the photographing environment parameter IE "posteroanterior view IE1", and the respiratory state parameter IB "exhalation IB1", for example, under the premise that, as the generation instruction information IF, the diagnostic region AR is the right lung field, the image analysis information IF1 is a luminance change value, and the statistical analysis information IF2 is an average value corresponds to parameter information IF30 shown in FIG. 8.

Although an example of the most simplified conceptual configuration of the parameter information IF3 is described herein, the photographing target parameter IO, the disease information parameter IS, the photographing environment parameter IE, and the respiratory state parameter IB are each actually configured by a plurality of types of attribute information. Although the photographing environment parameter IE and the respiratory state parameter IB are respectively described herein as the highest concept and the lowest concept, the highest and lowest concepts are not limited to these examples, and vary depending on a combination of types of attribute information.

In addition, the database 51 stores therein combinations of types of attribute information of not only the parameter information IF3 but also the diagnostic region AR, the image analysis information IF1, and the statistical analysis information IF2, and thus actually has a quite complex configuration.

The collection of the reference statistical values SV may be stored in the database 51 in such a manner that each piece of information indicated by the generation instruction information IF (IF1 to IF3) is provided with an attribute without performing grouping as described above, and the information storage apparatus 5 may have the following statistical processing function. That is to say, the information storage apparatus 5 may perform statistical processing using, from among the collection of the reference statistical values SV stored in the database 51, only information that matches the information indicated by the generation instruction information IF as information used as a population parameter in the statistical processing, and output the reference statistical value SV to be compared with a statistical analysis type of the first analysis value ANs indicated by the image analysis information IF1 and the statistical analysis information IF2.

<1-4-1-6. Display Image Generating Unit 600 and Display Unit 34>

The display image generating unit 600 performs display image generation processing to generate a diagnostic image IG2 so that the first analysis value ANs and the reference statistical value SV to be compared with the first analysis value ANs are displayed together. The display unit 34 performs processing to display the diagnostic image IG2. That is to say, the display unit 34 displays the first analysis value ANs and the reference statistical value SV together so that the first analysis value ANs and the reference statistical value SV can be compared with each other.

In addition, in a case where the user sets the diagnostic region AR while viewing the overall analysis image IG1 in the region setting processing, processing to generate the overall analysis image IG1 based on the overall analysis value AN is further performed in the display image generation processing, and the display unit 34 performs processing to display the overall analysis image IG1 before the statistical analysis processing is performed.

As illustrated in part (b) of FIG. 4, the overall analysis image IG1 in the present embodiment is an analysis still image configured as a still image based on the plurality of frame images SI (specifically, difference images SI' in a case where a luminance change value is used in the image analysis processing).

Figure 9:
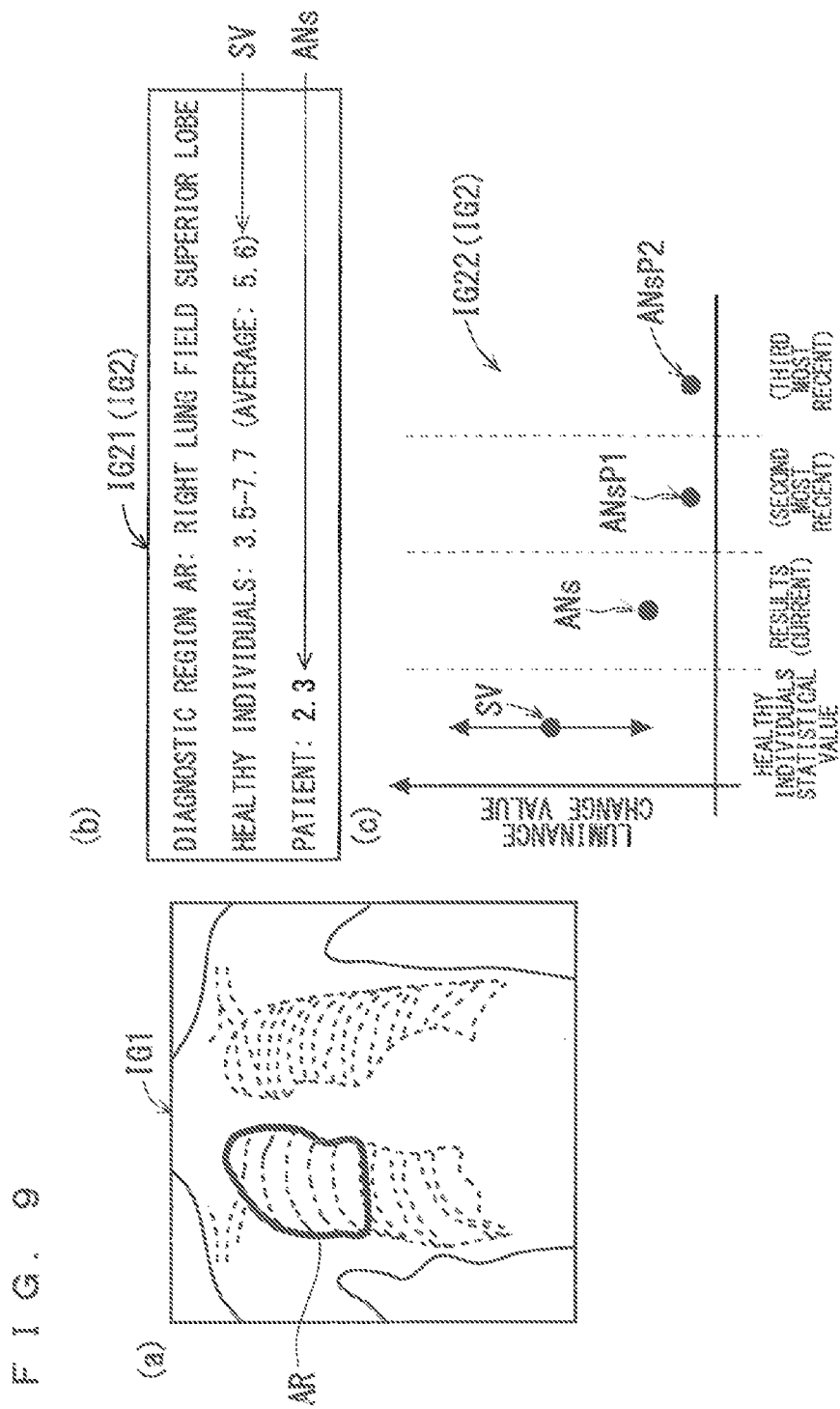
FIG. 9 is a schematic diagram for explaining an image generated in display image generation processing.

FIG. 9 is a schematic diagram for explaining that the display unit 34 displays the overall analysis image IG1 and the diagnostic image IG2 generated in the display image generation processing. Part (a) of FIG. 9 shows the overall analysis image (analysis still image) IG1, part (b) of FIG. 9 shows a diagnostic image IG21 (IG2) in which the reference statistical value SV and the first analysis value ANs are displayed as numerical values, and part (c) of FIG. 9 shows a diagnostic image IG22 (IG2) in which the reference statistical value SV and current and past first analysis values ANs are displayed in graphical form. Assumed herein is a case where the statistical analysis unit 500 provides the information storage apparatus 5 with conditions that, as the generation instruction information IF, the diagnostic region AR is the superior lobe of the right lung field (see part (a) of FIG. 9), the image analysis information IF1 is a luminance change value, and the statistical analysis information IF2 is an average value, and the photographing target parameter IO of the parameter information IF3 is the "healthy individual", and the information storage apparatus 5 returns the reference statistical value SV that meets these conditions to the display image generation processing.

As shown in part (a) of FIG. 9, this is the results of setting, as the diagnostic region AR, the superior lobe of the right lung field with respect to the analysis still image IG1. The set diagnostic region AR is displayed on the analysis still image IG1 so as not to obstruct display of the analysis still image IG1.

As shown in part (b) of FIG. 9, "2.3" that corresponds to the first analysis value ANs in the diagnostic image IG21 is an average value of the overall analysis value AN (luminance change value) in the diagnostic region AR (see part (a) of FIG. 9). On the other hand, "5.6" of "3.5-7.7 (AVERAGE: 5.6)" that corresponds to the reference statistical value SV is a numerical value indicating the average of average luminance change values in the diagnostic region AR calculated for a plurality of healthy individuals, and "3.5-7.7" indicates numerical values of a maximum value and a minimum value of the average luminance change values calculated for the healthy individuals. As described above, the reference statistical value SV generated using the healthy individuals as a population parameter and the first analysis value ANs of the test subject M who is a current target for diagnosis are displayed together to provide diagnosis support information that enables comparison with healthy individuals at a glance and understanding of the state of the test subject M. In a case where the first analysis value ANs is displayed as a numerical value as described above, a display color may be changed such that the first analysis value ANs is displayed in blue when it falls within a range between the maximum value and the minimum value of the average reference statistical values SV of the healthy individuals, and is displayed in red when it is out of the range, for example.

The diagnostic image IG2 may be either the diagnostic image IG21 displayed using numerical values as shown in part (b) of FIG. 9 or the diagnostic image IG22 displayed as a graph as shown in part (c) of FIG. 9. In either case, a numerical value of the first analysis value AVs obtained through the current analysis and the reference statistical value SV are displayed so that the first analysis value AVs relative to values of the healthy individuals can be known at a glance. As shown in part (c) of FIG. 9, as the first analysis value ANs, not only the results of the current analysis but also the results of the past analysis, such as the second most recent first analysis value ANsP1 and the third most recent first analysis value ANsP2, of the test subject M as the target for diagnosis may be displayed along with the reference statistical value SV by providing a function to hold the results of the past analysis of the test subject M. In the case of part (c) of FIG. 9, the first analysis value becomes closer to the reference statistical value SV of the healthy individuals in the order of the third most recent first analysis value ANsP2, the second most recent first analysis value ANsP1, and the current first analysis value ANs, and thus it seems that the patient is recovering. With this structure, the course from the past (whether it has become better or worse) can be understood at a glance.

On the other hand, in a case where the reference statistical value SV is generated using patients with a particular disease, such as "patients with COPD", of the photographing target parameter IO of the parameter information IF3 as a population parameter, the reference statistical value SV and the first analysis value ANs are displayed together so that the first analysis value ANs can be compared with values of the patients with the disease at a glance. That is to say, if the first analysis value ANs falls within a range of the reference statistical value SV of the patients with COPD in which COPD is identified, the possibility that the target subject M is suffering from COPD is suggested.

As described above, the information storage apparatus 5 outputs the reference statistical value SV generated using only information that matches the information indicated by the generation instruction information IF as a population parameter in the statistical processing. If attribute information that matches the conditions of the parameter information IF3 and the diagnostic region AR is not stored in the database 51, normalization can be performed using attribute information stored in the database 51 to generate the reference statistical value SV that matches the conditions.

The above-mentioned normalization is performed, for example, in a case where the reference statistical value SV is desired to be generated using the body thickness as a condition because there is only information on the body thickness as information of the test subject M as the current target for diagnosis, but, although the weight and the height are stored, the body thickness is not stored as the attribute information of the photographing target parameter IO in the database 51. That is to say, the information storage apparatus 5 can newly calculate the body thickness based on the weight and the height as the attribute information of the photographing target parameter IO, and collate the calculated body thickness and the body thickness of the test subject M to output the reference statistical value SV of individuals having the weight and the height that match the conditions from the collection of the reference statistical values SV stored in the database 51.

As described above, the information storage apparatus 5 may be configured to be able to derive the corresponding attribute information by performing any calculation processing (normalization) even if the corresponding attribute information is not stored in the database 51.

<1-5. Basic Operation of Image Processing Apparatus 3>

Figure 10:
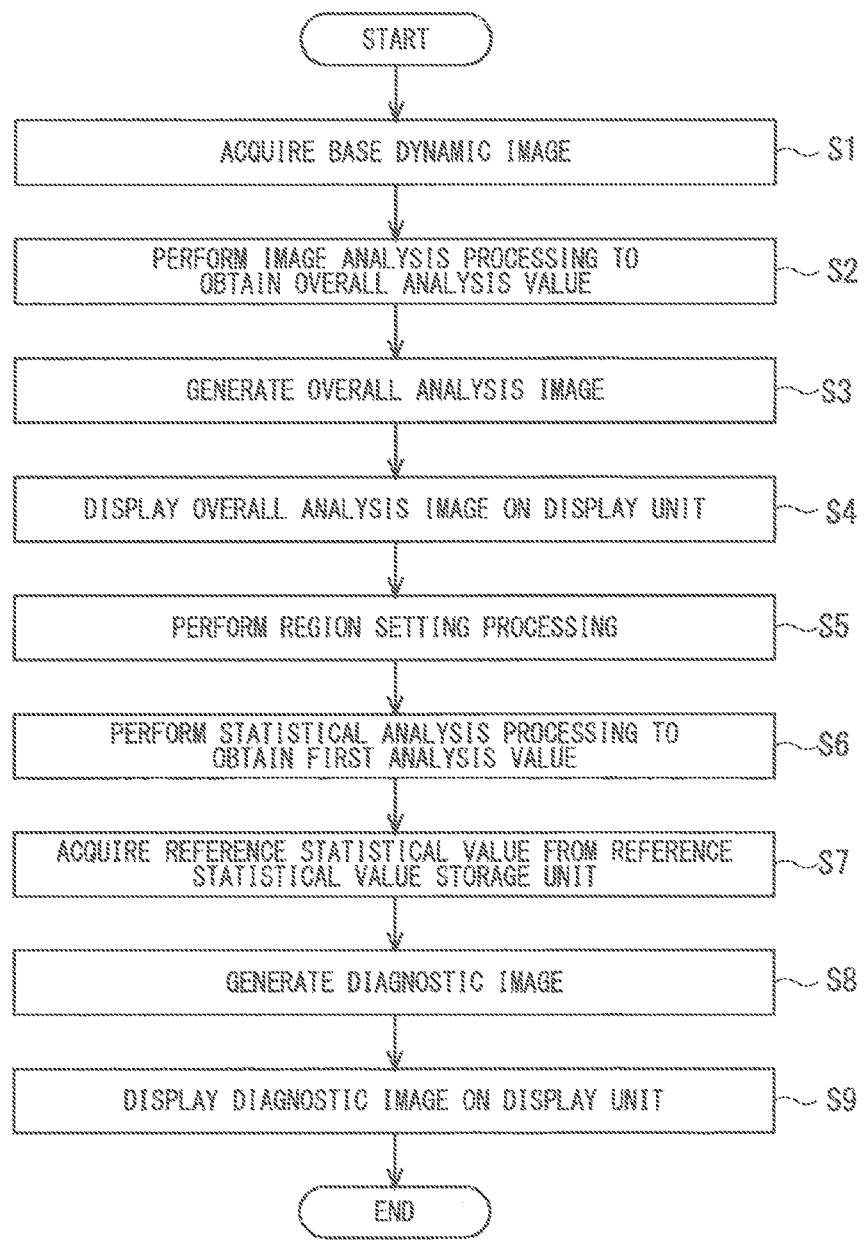
FIG. 10 is a flowchart for explaining a basic operation of the image processing apparatus 3 achieved in Embodiment 1.

FIG. 10 is a flowchart for explaining a basic operation achieved by the image processing apparatus 3 according to the present embodiment. Since an individual function of each unit has already been described (see FIG. 2), only an overall flow is described herein.

As shown in FIG. 10, in Step S1, the base dynamic image acquiring unit 200 of the control unit 31 first acquires the base dynamic image (plurality of frame images SI) photographed by the reading control device 14 of the photographing apparatus 1 through the photographing control apparatus 2 (see FIG. 3).

In Step S2, the image analysis unit 300 performs the image analysis processing on the plurality of frame images SI acquired in Step S1 to obtain the overall analysis value AN (see FIG. 4).

In Step S3, the display image generating unit 600 generates the overall analysis image (analysis still image) IG1 based on the overall analysis value AN obtained in Step S2.

In Step S4, the display unit 34 displays the analysis still image IG1 generated in Step S3 (see part (a) of FIG. 9).

In Step S5, the region setting unit 400 performs the region setting processing by the user designating the diagnostic region AR via the operation unit 33 with respect to the analysis still image IG1 displayed in Step S4 (see part (a) of FIG. 9).

In Step S6, the statistical analysis unit 500 selectively performs the statistical analysis processing on the diagnostic region AR set in Step S5 to obtain the first analysis value ANs, and outputs the generation instruction information IF (diagnostic region AR, image analysis information IF1, statistical analysis information IF2, and parameter information IF3) to the information storage apparatus 5 (see FIG. 2).

In Step S7, upon receiving the generation instruction information IF output in Step S6, the information storage apparatus 5 generates the reference statistical value SV that matches the condition of the generation instruction information IF from the collection of the reference statistical values SV stored in the database 51.

In Step S8, the display image generating unit 600 generates the diagnostic image IG2 so that the first analysis value ANs obtained in Step S6 and the reference statistical value SV obtained in Step S7 are displayed together (see parts (b) and (c) of FIG. 9).

The diagnostic image IG2 may be generated using numerical values as shown in part (b) of FIG. 9 or may be generated as a graph as shown in part (c) of FIG. 9.

Finally, in Step S9, the display image generating unit 600 outputs the diagnostic image IG2 generated in Step S8 to the display unit 34 (see parts (b) and (c) of FIG. 9), and the flowchart of this operation ends.

As described above, the image processing apparatus 3 according to Embodiment 1 performs the statistical analysis processing using the overall analysis value AN obtained by performing the image analysis processing on the plurality of frame images SI constituting the base dynamic image to obtain the first analysis value ANs, and displays the first analysis value ANs and the reference statistical value SV to be compared with the first analysis value ANs together. That is to say, the first analysis value ANs of the body of the test subject M (a target object) as the current target for diagnosis and the reference statistical value SV calculated using reference dynamic images of a plurality of past test subjects other than the test subject M can be displayed simultaneously. As a result, a difference from the reference statistical value SV calculated from the past target subjects can be understood at a glance, and thus the diagnosis support information for the user such as a doctor can be provided. Consequently, time required for diagnosis can be reduced, and diagnosis of dynamics can be made properly and efficiently.

The region setting processing to set the diagnostic region AR from the lung field region is performed. This allows the user to set a desired region (e.g., a region with any abnormality) as the diagnostic region AR. The statistical analysis unit 500 selectively performs the statistical analysis processing using part of the overall analysis value AN in the diagnostic region AR set in the region setting processing to obtain the first analysis value ANs. That is to say, the first analysis value ANs in the diagnostic region AR and the reference statistical value SV in the diagnostic region AR can be obtained. For example, in a case where there is any abnormality only in a region of the lung field region on which the image analysis processing has been performed, the region with the abnormality can be set as the diagnostic region AR to obtain the first analysis value ANs that is effective in diagnosis and to obtain the reference statistical value SV that is specific to the region with the abnormality. That is to say, since the first analysis value ANs and the reference statistical value SV vary depending on a set region, information that is proper and significant in diagnosis can be obtained by narrowing down the diagnostic region AR.

Furthermore, the display unit 34 performs processing to display the overall analysis image based on the overall analysis value AN, and the overall analysis image is the analysis still image IG1 configured as a still image based on the plurality of frame images SI. This allows the user to set a desired region (e.g., a region with any abnormality) as the diagnostic region AR while viewing the analysis still image IG1. If the analysis still image IG1 and the diagnostic image IG2 are viewed simultaneously, the first analysis value ANs and the reference statistical value SV can be compared with each other, and an abnormality and the like can be identified also on the analysis still image IG1.

The reference statistical value SV includes a statistical value obtained after classification using, as a population parameter, at least one of the photographing target parameter IO, the disease information parameter IS, the photographing environment parameter IE, and the respiratory state parameter IB of the parameter information IF3. That is to say, a proper reference statistical value SV can be selected for display depending on the purpose of diagnosis from a plurality of patterns of statistical values calculated by changing the population parameter among the above-mentioned four parameters or combinations of any of the above-mentioned four parameters. For example, in a case where the target object as a target for diagnosis is a healthy individual, a statistical value calculated by using, as the population parameter, a plurality of healthy individuals is used as the reference statistical value SV, whereas, in a case where the target object as the target for diagnosis is a patient with a particular disease, a statistical value calculated by using, as the population parameter, a plurality of patients with the particular disease can be used as the reference statistical value SV. As described above, the population parameter used to calculate the reference statistical value SV can be changed depending on the purpose of diagnosis.

At least one of the luminance change value, the distance indicating the size of the target region, the coordinates of the particular position, the area of the target region, and the moving amount of the particular position is calculated in the image analysis processing. That is to say, as with the first analysis value ANs, the second analysis values and the reference statistical value SV are calculated as the above-mentioned values. As a result, the first analysis value ANs that varies depending on diagnosis can be calculated. As described above, the diagnosis support information that is effective to the user can be provided.

The reference statistical value SV is at least one of an average value, a maximum value, a minimum value, a range between the maximum value and the minimum value, and a degree of variation of the second analysis values obtained by performing processing similar to the image analysis processing and the statistical analysis processing on reference dynamic images of a plurality of past test subjects, and thus judgement on whether the lung field region is normal or not can efficiently be made when the reference statistical value SV is compared with the first value ANs. As a result, the diagnosis support information that is effective to the user can be provided.

The target region is the lung field region, and thus diagnosis of dynamics on whether the lung field region is abnormal or not can be made while comparison with the reference statistical value SV is made. As a result, a region with any abnormality of the lung field region can efficiently be determined, time required for diagnosis of dynamics can be reduced, and diagnosis of dynamics can be made properly and efficiently.

<2. Embodiment 2>

An image processing apparatus 3' in Embodiment 2 of the present invention configures the overall analysis image IG1 as a dynamic image in contrast to the image processing apparatus 3 in Embodiment 1, and thus has been changed to include a region setting unit 400', a statistical analysis unit 500', a reference statistical value generating unit 550', and a display image generating unit 600' (not illustrated) as described below. The remaining components are similar to those of the image processing apparatus 3.

Figure 11:
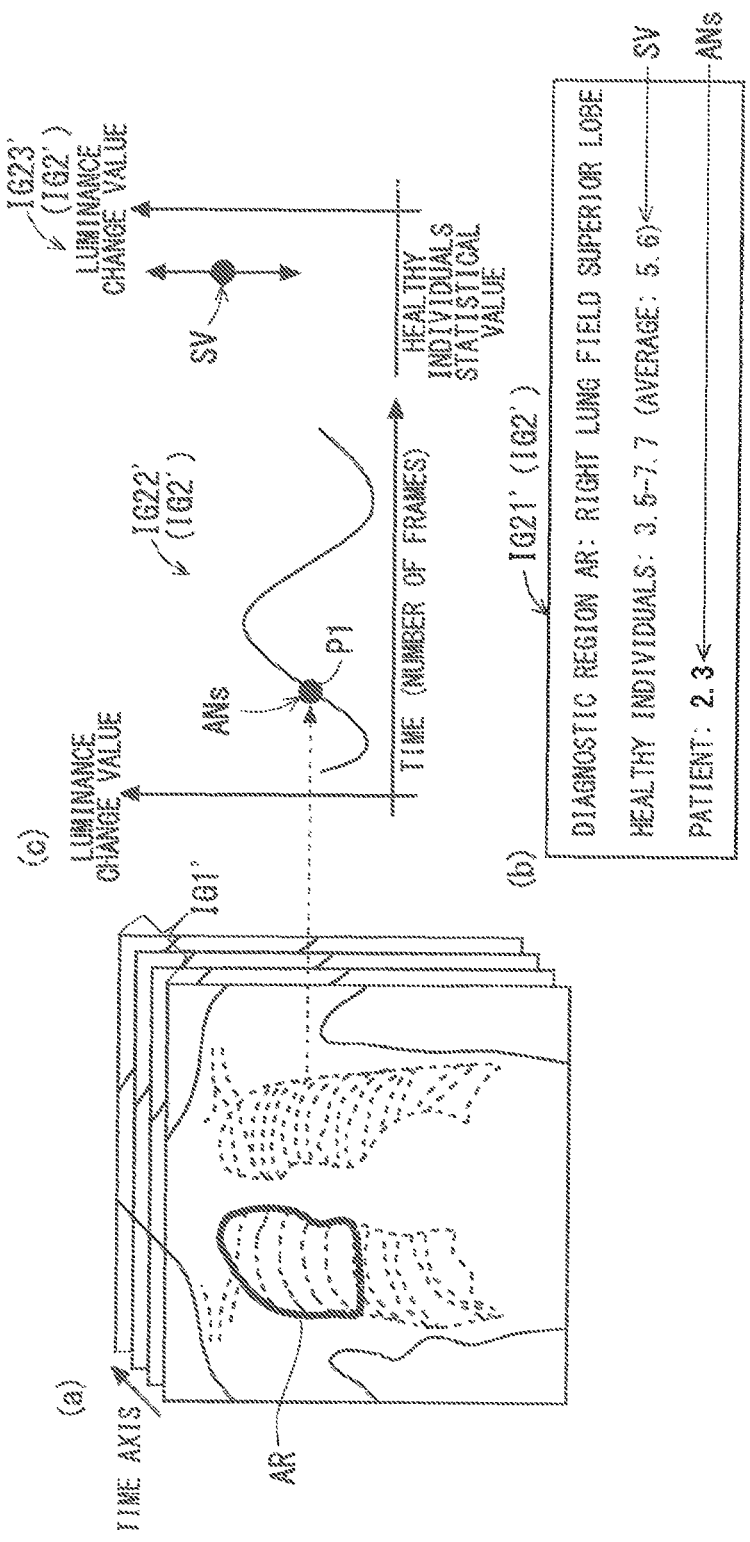
FIG. 11 is a schematic diagram for explaining display image generation processing in Embodiment 2.

FIG. 11 is a schematic diagram showing an overall analysis image IG1' (part (a) of FIG. 11) and diagnostic images IG21' to IG23' (IG2') (parts (b) and (c) of FIG. 11) generated by the display image generating unit 600' (in the display image generation processing). In FIG. 11, a case where the overall analysis value AN, the first analysis value ANs, and the reference statistical value SV are each a luminance change value is assumed, a graph of the diagnostic image IG22' of part (c) of FIG. 11 shows the first analysis value ANs, a graph of the diagnostic image IG23' of part (c) of FIG. 11 shows the reference statistical value SV, and the vertical axis of each of the graphs indicates the luminance change value. The horizontal axis of the graph of the diagnostic image IG22' indicates photographing time.

Only functions different from those in Embodiment 1 are described below with reference to FIG. 11.

<2-1. Region Setting Unit 400' and Display Image Generating Unit 600'>

Image analysis processing similar to that performed by the image analysis unit 300 is performed to obtain the overall analysis value AN in the lung field region as a whole, but the display image generating unit 600' generates the overall analysis image IG1' that is an analysis dynamic image configured as a dynamic image based on the plurality of frame images SI. That is to say, processing to generate the analysis dynamic image IG1 (overall analysis image) based on the overall analysis value AN is performed in the display image generation processing, and the display unit 34 performs processing to display the analysis dynamic image IG1 before the statistical analysis processing is performed.

The region setting unit 400' performs the region setting processing on each of the frame images constituting the analysis dynamic image IG1'. The frame images constituting the analysis dynamic image IG1' refer to the above-mentioned difference images SI' in a case where the overall analysis value AN is (i) the luminance change value and (v) the moving amount of the particular position described above (see, FIG. 4), and refer to the above-mentioned frame images SI in a case where the overall analysis value AN is (ii) the distance indicating the size of the lung field region, (iii) the coordinates of the particular position, and (iv) the area of the lung field region described above (see, for example, FIG. 5).

In a case where the user designates the diagnostic region AR via the operation unit 33, the user may designate the diagnostic region AR for each of the frame images SI (or difference images SI') constituting the analysis dynamic image IG1', but a method in which the user designates the diagnostic region AR for only first one of the frame images SI (or difference images SI') constituting the analysis dynamic image IG1', for example, and the diagnostic region AR is automatically set for the remaining frame images SI (or difference images SI') is efficient.

The shape of the lung field region, however, varies depending on the frame image SI. Display of the diagnostic region AR on the overall analysis image IG1 varies accordingly. Therefore, the shape of the lung field region varies depending on a change in respiratory state and the effects of heart beat, for example, and the first analysis value ANs can be obtained in accordance with the range of the diagnostic region AR. The diagnostic region AR is thus required to be set accurately. In order to set the diagnostic region AR, for example, movement of the lung field region is tracked and associated among the frame images SI (or difference images SI') to automatically obtain the diagnostic region AR. As a method for tracking and associating the movement among the frame images SI (or difference images SI'), an existing method such as corresponding point search processing can be used.

<2-2. Statistical Analysis Unit 500' and Reference Statistical Value Generating Unit 550'>

The statistical analysis unit 500' performs the statistical analysis processing on the diagnostic region AR set for each of the frame images SI (or difference images SI') constituting the analysis dynamic image IG1'. That is to say, the first analysis value ANs is a plurality of first analysis values calculated based on the plurality of frame images SI (or difference images SI'), and is obtained for each of the frame images SI (or difference images SI'). The statistical analysis unit 500' outputs the generation instruction information IF to the reference statistical value generating unit 550'.

The plurality of first analysis values ANs are, for example, a plurality of luminance change values that are average values of luminance change values in the diagnostic region AR of each of the plurality of frame images.

When the generation instruction information IF is input from the statistical analysis unit 500', the reference statistical value generating unit 550' generates the reference statistical value SV that meets the conditions. The reference statistical value SV is herein a single statistical value as in Embodiment 1. That is to say, the second analysis value is a single value obtained using all the frame images constituting the reference dynamic images, and is not a plurality of values calculated for respective frame images as with the first analysis value ANs.

<2-3. Display Image Generating Unit 600'>

The display image generating unit 600' then performs the display image generation processing to generate a diagnostic image IG2' (IG21' to IG23') so that the plurality of first analysis values ANs and the reference statistical value SV generated by the reference statistical value generating unit 550' are displayed together.

In the display image generation processing, the plurality of first analysis values ANs are sequentially displayed in accordance with photographing time of the plurality of frame images SI to display the analysis dynamic image IG1' (see part (a) of FIG. 11) and the first analysis values ANs (see part (b) of FIG. 11) in association with each other in terms of time to thus perform processing to generate the diagnostic image IG2'. This is achieved by outputting, to the display image generating unit 600', the overall analysis value AN from the image analysis unit 300' and the first analysis values ANs from the statistical analysis unit 500' in association with each other in terms of time (while holding time information).

In the display image generation processing, processing to generate a graph (the diagnostic image IG22') obtained by plotting the plurality of first analysis values ANs in a direction of the photographing time is further performed (see part (c) of FIG. 11). That is to say, the diagnostic image IG22' is a graph showing a change of the first analysis value ANs over time, and the graph is associated with the analysis dynamic image IG1' in terms of time (see parts (a) and (c) of FIG. 11). On the graph of the diagnostic image IG22', a point P1 is plotted so that correspondence to a display frame of the analysis dynamic image currently being displayed can easily be known. As a result, comparison with healthy individuals can be made at a glance by comparing the point P1 and the reference statistical value SV of the healthy individuals shown in the diagnostic image IG23'.

Finally, the display image generating unit 600' outputs the diagnostic image IG2' (IG21' to IG23') to the display unit 34, and the display unit 34 displays the diagnostic image IG2'.

As a result, as playback and display of the analysis dynamic image IG1' shown in part (a) of FIG. 11 changes over time, the first analysis value ANs shown in the diagnostic image IG21' of part (b) of FIG. 11 and the first analysis value ANs on the graph of the diagnostic image IG22' of part (c) of FIG. 11 change in synchronization with the change in playback and display of the analysis dynamic image IG1'. Since the reference statistical value SV is a single statistical value as in Embodiment 1, the reference statistical value SV is fixed in the diagnostic images IG21' and IG23' (see parts (b) and (c) of FIG. 11.

As described above, in the image processing apparatus 3' according to Embodiment 2, the display unit 34 further performs processing to display the overall analysis image based on the overall analysis value AN, and the overall analysis image is the analysis dynamic image IG1' configured as a dynamic image based on the plurality of frame images. This allows the user to set a desired region (e.g., a region with any abnormality) as the diagnostic region AR while viewing the analysis dynamic image IG1'. If the analysis dynamic image IG1' and the diagnostic image IG2' are viewed simultaneously, the plurality of first analysis values ANs and the reference statistical value SV can be compared with each other, and an abnormality and the like can be identified also on the analysis dynamic image IG1'.

The display unit 34 further performs processing to sequentially display the plurality of first analysis values ANs in accordance with the photographing time of the plurality of frame images to display the analysis dynamic image IG1' and the plurality of first analysis values ANs in association with each other in terms of time. That is to say, display of the first analysis value ANs can be changed in synchronization with the change of the analysis dynamic image IG1' over time. As a result, diagnosis on a time period in which an abnormality occurs, a time period in which the abnormality disappears (returns to normal), and the like can be made in consideration of a time axis. As a result, a change of a two-dimensional space on the frame images over time can visually be captured while it is compared with the reference statistical value SV.

The display unit 34 further performs processing to display the graph obtained by plotting the plurality of first analysis values ANs in the direction of the photographing time, and the graph is associated with the analysis dynamic image IG1' in terms of time. For example, if the graph is displayed so that a frame image of the analysis dynamic image IG1' currently being displayed can be known (e.g., the point P1 of part (c) of FIG. 11), the position (time) on the graph to which the frame image currently being displayed corresponds can be understood at a glance in synchronization with the change of display of the analysis dynamic image IG1' and the first analysis value ANs over time. As a result, time at which any abnormality occurs can be identified on the graph.

<2-4. Modification of Embodiment 2>

In Embodiment 2 described above, the reference statistical value SV is a single statistical value that is fixed in the diagnostic images IG21' and IG23', but the reference statistical value SV may be displayed so as to change over time.

The structure of Modification of Embodiment 2, however, is based on the premise that the reference statistical value SV is held in the database 51 as a plurality of reference statistical values SV corresponding to the plurality of first analysis values ANs, as a case where the plurality of first analysis values ANs and the reference statistical value SV are synchronized with each other is assumed.

Under such a condition, the statistical analysis unit 500' outputs the generation instruction information IF to the reference statistical value generating unit 550 for each of the frame images SI (or difference images SI'), for example. When the generation instruction information IF is input from the statistical analysis unit 500', the reference statistical value generating unit 550' sequentially generates the reference statistical values SV that meet these conditions, and outputs the reference statistical values SV to the display image generating unit 600'. In the display image generation processing, processing to generate the diagnostic images IG21' to IG23' (IG2') so that the reference statistical values SV are sequentially displayed in accordance with the plurality of first analysis values ANs is performed.

As a result, as playback and display of the analysis dynamic image IG1' shown in part (a) of FIG. 11 changes over time, the first analysis value ANs and the reference statistical value SV shown in the diagnostic image IG21' of part (b) of FIG. 11 and the first analysis value ANs on the graph of the diagnostic image IG22' of part (c) of FIG. 11 and the reference statistical value SV shown in the diagnostic image IG23' of part (c) of FIG. 11 change in synchronization with the change in playback and display of the analysis dynamic image IG1'.

As described above, in the image processing apparatus according to Modification of Embodiment 2, the diagnostic image IG2' is generated so that the plurality of reference statistical values SV are sequentially displayed in accordance with the plurality of first analysis values ANs in the display image generation processing. That is to say, the analysis dynamic image IG1', the first analysis values ANs, and the reference statistical values SV can be displayed in association with one another in terms of time. As a result, not only display of the first analysis value ANs but also display of the reference statistical value SV can be changed in synchronization with the change of the analysis dynamic image IG1' over time. Since comparison with the reference statistical value SV that varies depending on the photographing time can be made, more detailed diagnosis of dynamics can be made.

<3. Embodiment 3>

Figure 12:
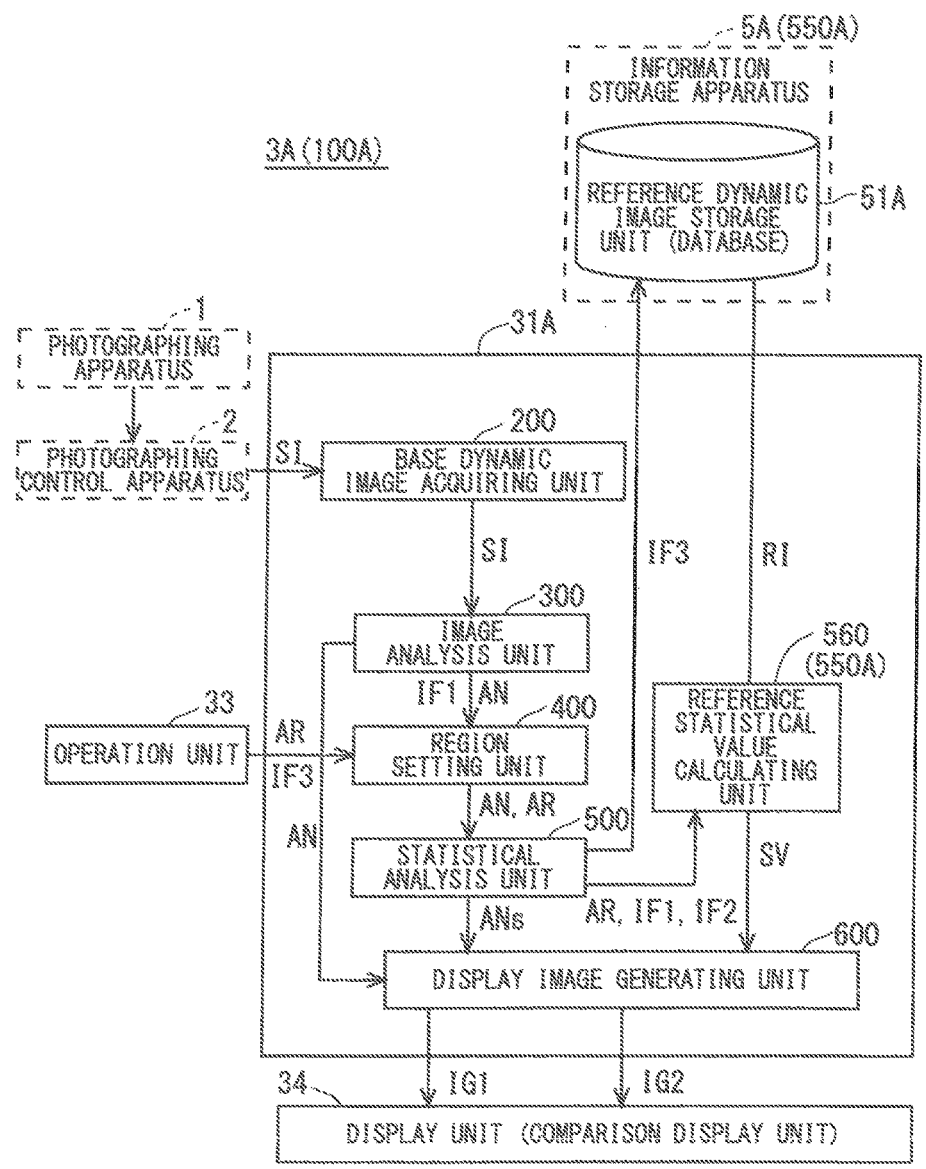
FIG. 12 is a block diagram showing a functional configuration of an image processing apparatus 3A according to Embodiment 3.

FIG. 12 is a diagram showing a functional configuration of a control unit 31A of an image processing apparatus 3A according to Embodiment 3 of the present invention. The control unit 31A is used as an alternative to the control unit 31 (see FIG. 2) of the image processing apparatus 3 in Embodiment 1. Embodiment 3 is different from Embodiment 1 in that, due to a change to a reference statistical value generating unit 550A, an information storage apparatus 5A includes a reference dynamic image storage unit 51A, and the control unit 31A further includes a reference statistical value calculating unit 560. The remaining components are similar to those of the image processing apparatus 3.

<3-1. Reference Statistical Value Generating Unit 550A>

The reference statistical value generating unit 550A in Embodiment 3 includes the reference dynamic image storage unit 51A and the reference statistical value calculating unit 560.

When the generation instruction information IF is input from the statistical analysis unit 500 (see FIG. 12), the information storage apparatus 5A outputs a plurality of reference dynamic images RI that meet the parameter information IF3 from the database 51A to the reference statistical value calculating unit 560 based on the parameter information IF3.

The reference statistical value calculating unit 560 performs image analysis processing and statistical analysis processing similar to those performed to obtain the first analysis value ANs using the reference dynamic images RI input from the reference dynamic image storage unit 51A, the diagnostic region AR, the image analysis information IF1, and the statistical analysis information IF2 input from the statistical analysis unit 500 to calculate and generate the reference statistical value SV to be compared with the first analysis value ANs.

<3-2. Basic Operation of Image Processing Apparatus 3A>

Figure 13:
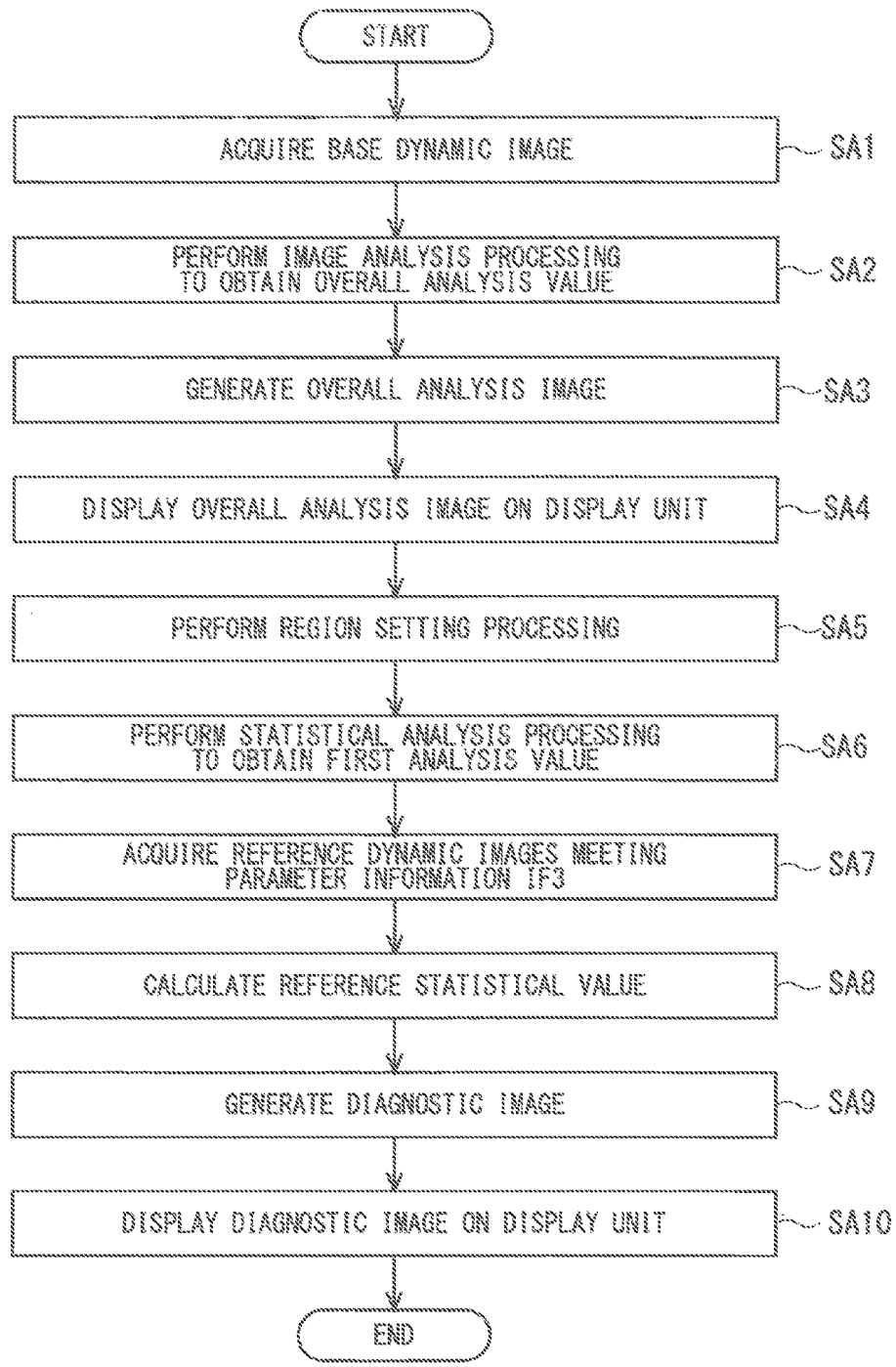
FIG. 13 is a flowchart for explaining a basic operation of the image processing apparatus 3A achieved in Embodiment 3.

FIG. 13 is a flowchart showing operation of the image processing apparatus 3A according to Embodiment 3. Steps SA1 to SA6, SA9, and SA10 of FIG. 13 are similar to Steps S1 to S6, S8, and S9 of FIG. 10, and thus description thereof is omitted.

In Embodiment 3, the reference statistical value generating unit 550 (information storage apparatus 5) has been replaced with the reference statistical value generating unit 550A (information storage apparatus 5A and reference statistical value calculating unit 560), and thus the reference statistical value storage unit 51 has been changed to the reference dynamic image storage unit 51A, and the reference statistical value calculating unit 560, which is not included in Embodiment 1, has been added to change only the following steps.

That is to say, after Steps SA1 to SA6, which are similar to those in Embodiment 1, in Step SA7 as shown in FIG. 13, the reference dynamic image storage unit 51A outputs the reference dynamic images RI that meet the parameter information IF3 based on the parameter information IF3 input in Step SA6 to the reference statistical value calculating unit 550A, and the statistical analysis unit 500 inputs the diagnostic region AR, the image analysis information IF1, and the statistical analysis information IF2 into the reference statistical value calculating unit 560 (see FIG. 12).

In Step SA8, the reference statistical value calculating unit 560 performs image analysis processing and statistical analysis processing similar to those performed to obtain the first analysis values ANs using the reference dynamic images RI, the diagnostic region AR, the image analysis information IF1, and the statistical analysis information IF2 input in Step SA7 to calculate the reference statistical value SV, and outputs the reference statistical value SV to the display image generating unit 600 (see FIG. 12). The remaining steps are similar to those in Embodiment 1.

As described above, in the image processing apparatus 3A according to Embodiment 3, the reference statistical value calculating unit 560 can calculate the reference statistical value SV for display based on the parameter information IF3 depending on the purpose of diagnosis by changing the population parameter of the reference dynamic images RI used to calculate the reference statistical value SV. For example, in a case where a target for diagnosis is a healthy individual, a statistical value calculated using reference dynamic images RI of a plurality of healthy individuals as a population parameter can be used as the reference statistical value SV, whereas, in a case where the target for diagnosis is a patient with a particular disease, a statistical value calculated using reference dynamic images RI of a plurality of patients with the particular disease as a population parameter can be used as the reference statistical value SV. As described above, the population parameter of the reference dynamic images RI used to calculate the reference statistical value SV can be changed depending on the purpose of diagnosis.

The image processing apparatus 3A according to Embodiment 3 is described based on Embodiment 1 in which the overall analysis image includes the analysis still image IG1, but may be changed based on Embodiment 2 in which the overall analysis image includes the analysis dynamic image IG1'.

<4. Modifications>

Embodiments of the present invention have been described so far, but the present invention is not limited to the above-mentioned embodiments, and various modifications can be made on the above-mentioned embodiments.

Although the image processing apparatuses 3, 3', and 3A are described separately in the present embodiments so as to be implemented individually, individual functions of the image processing apparatuses 3, 3', and 3A may be combined with one another unless any contradiction occurs.

The image processing apparatuses 3, 3', and 3A according to the present embodiments have been described based on the premise that one type of first analysis value ANs and one type of reference statistical value SV are calculated, but a plurality of types of first analysis values ANs and a plurality of types of reference statistical values SV may be calculated.

A method enabling calculation of a plurality of types of first analysis values ANs and switching of a method for displaying each of the types of first analysis values ANs depending on the application of the user is described below.

Figure 14:
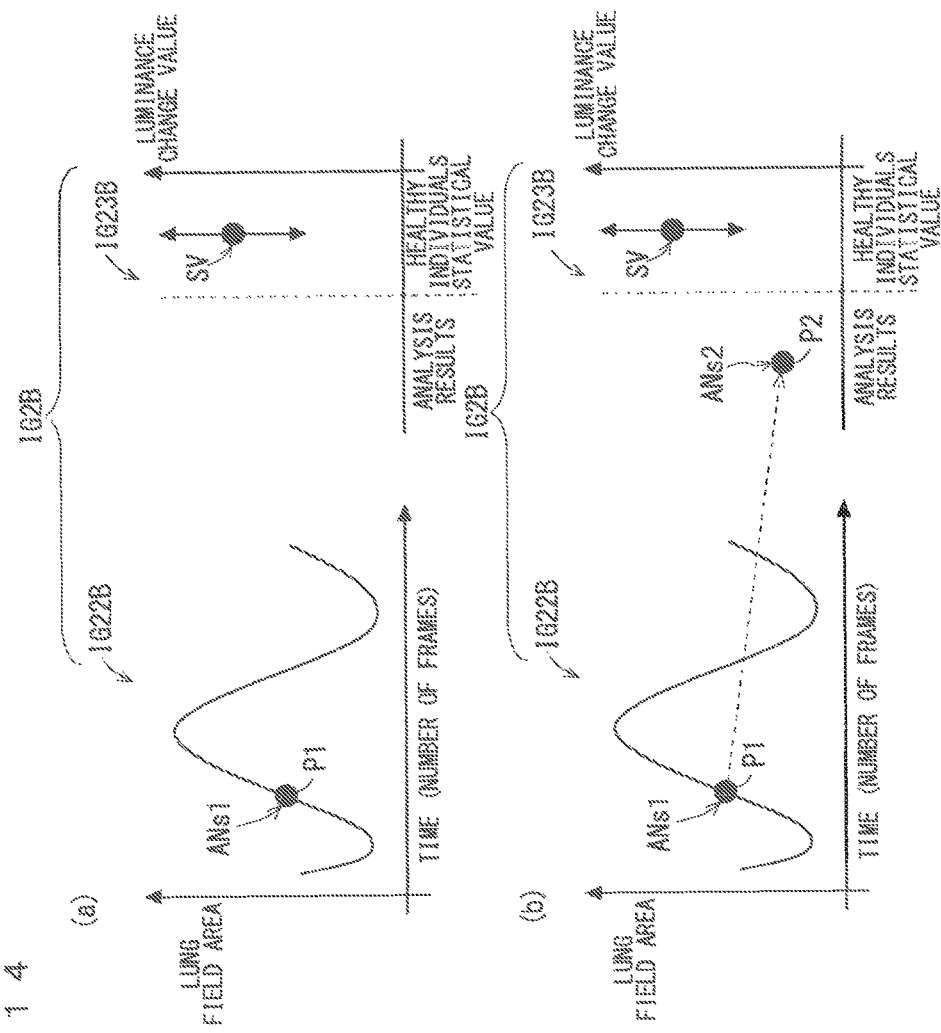
FIG. 14 is a schematic diagram for explaining an example of a display method enabling switching among a plurality of types of first analysis values.

FIG. 14 is a schematic diagram showing a diagnostic image IG2B including a partial diagnostic image IG22B and a partial diagnostic image IG23B generated in the display image generation processing. In FIG. 14, the reference statistical value SV is a statistical value obtained using healthy individuals as a target and is shown in the partial diagnostic image IG23B, and, in a graph of the partial diagnostic image IG22B of FIG. 14, the vertical axis indicates the above-mentioned (iv) area of the lung field region and the horizontal axis indicates photographing time. The vertical axis in a graph of the partial diagnostic image IG23B of FIG. 14 indicates the above-mentioned (i) luminance change value.

In the example of FIG. 14, the image analysis processing is performed with respect to two types of values, namely, the above-mentioned (i) luminance change value and (iv) area of the lung field region, and the overall analysis value AN1 corresponding to the area of the lung field region and the overall analysis value AN2 corresponding to the luminance change value are obtained in the image analysis processing.

The statistical analysis processing is selectively performed using part of the overall analysis values AN1 and AN2 in the diagnostic region AR set in the region setting processing to obtain two types of first analysis values ANs1 and ANs2. The first analysis value ANs1 herein corresponds to the area of the lung field region, and the first analysis value ANs2 herein corresponds to the luminance change value.

Under designation of the user via the operation unit 33, the display image generation processing is performed so that the first analysis value ANs1 corresponding to the area of the lung field region is displayed in the graph of the partial diagnostic image IG22B, and the first analysis value ANs2 corresponding to the luminance change value is eventually plotted in the partial diagnostic image IG23B, for example.

As a result, even in a case where the graph of the partial diagnostic image IG22B shows what is different from the reference statistical value SV of healthy individuals of the partial diagnostic image IG23B (in part (a) of FIG. 14, the graph of the partial diagnostic image IG22B shows the area of the lung field, i.e., the first analysis value ANs1, and the reference statistical value SV of healthy individuals of the partial diagnostic image IG23B is the luminance change value, and the first analysis value ANs2 is initially omitted), a display method can be switched so that the first analysis value ANs is an analysis value that can be compared with the reference statistical value SV (in part (b) of FIG. 14, the point P1 of the first analysis value ANs1 is separately included in the partial diagnostic image IG23B as a point P2 of a luminance change value, i.e., the first analysis value ANs2, that can be compared with the reference statistical value SV of healthy individuals).

As described above, the image analysis processing can be performed with respect to a plurality of types of values from among the luminance change value, the distance indicating the size of the target region, the coordinates of the particular position, the area of the target region, and the moving amount of the particular position to calculate a plurality of types of first analysis values ANs. As a result, the lung field region can comprehensively be diagnosed from various perspectives. As described above, the diagnosis support information that is effective to the user can be provided.

The image processing apparatuses 3, 3', and 3A according to the present embodiments each include the region setting unit 400, but may not include the region setting unit 400. That is to say, the statistical analysis unit 500 selectively performs the statistical analysis processing using part of the overall analysis value AN in the diagnostic region AR set in the region setting processing to obtain the first analysis value ANs, but, in a case where the region setting unit 400 is not included, the statistical analysis processing is performed using the entire region obtained through analysis as the diagnostic region AR (overall analysis value AN), for example, to obtain the first analysis value ANs.

The subject (target object) M is not limited to the human body, and may be the body of an animal.

While the present invention has been described in detail, the foregoing description is in all aspects illustrative and not restrictive. It is therefore understood that numerous modifications that have not been described can be devised without departing from the scope of the present invention.

The invention claimed is:
1. An image processing apparatus comprising:
   a controller with a central processing unit configured to
      acquire a base dynamic image obtained by sequentially photographing, in a time direction, a state of a dynamic period in which a physical state of a target region in a body of a target object changes periodically, the target object being a human or an animal;
      perform image analysis processing on a plurality of frame images constituting said base dynamic image to obtain an overall analysis value in said target region as a whole;
      perform statistical analysis processing on a diagnostic region using said overall analysis value to obtain a first analysis value representing said diagnostic region, the diagnostic region being a whole or part of said target region; and
      output, based on generation instruction information, a reference statistical value calculated using reference dynamic images of a plurality of past target objects, wherein the generation instruction information includes a population parameter that designates a subset of the reference dynamic images from which the reference statistical value is calculated; and
   a display for displaying said first analysis value and said reference statistical value together, wherein
   the population parameter includes at least one of:
      a photographing target parameter indicating information specific to said plurality of target objects;
      a disease information parameter indicating presence or absence of a disease and a state of the disease of said plurality of target objects; and
      a photographing environment parameter indicating photographing environments in which said reference dynamic images have been photographed.

2. The image processing apparatus according to claim 1, the controller further configured to
   perform region setting processing to set said diagnostic region from said target region, wherein
   said statistical analysis processing is selectively performed using part of said overall analysis value in said diagnostic region set in said region setting processing to obtain said first analysis value.

3. The image processing apparatus according to claim 1, wherein
   said display further performs processing to display an overall analysis image based on said overall analysis value, and
   said overall analysis image includes an analysis still image configured as a still image based on said plurality of frame images.

4. The image processing apparatus according to claim 1, wherein
   said display further performs processing to display an overall analysis image based on said overall analysis value, and
   said overall analysis image is based on said plurality of frame images.

5. The image processing apparatus according to claim 4, wherein
   said first analysis value includes a plurality of first analysis values calculated based on said plurality of frame images, and
   said display further performs processing to sequentially display said plurality of first analysis values in accordance with photographing time of said plurality of frame images to display said analysis dynamic image and said plurality of first analysis values in association with each other in terms of time.

6. The image processing apparatus according to claim 5, wherein
   said display further performs processing to display a graph obtained by plotting said plurality of first analysis values in a direction of said photographing time, and
   said graph is associated with said analysis dynamic image in terms of time.

7. The image processing apparatus according to claim 1, wherein
   said image analysis processing includes processing to calculate at least one of:
      a luminance change value in corresponding pixels of said plurality of frame images;
      a distance indicating a size of said target region in each of said plurality of frame images;
      coordinates of a particular position in said target region in each of said plurality of frame images;
      an area of said target region in each of said plurality of frame images; and
      a moving amount of said particular position among said plurality of frame images.

8. The image processing apparatus according to claim 1, wherein
said reference statistical value includes at least one of an average value, a maximum value, a minimum value, a range between said maximum value and said minimum value, and a degree of variation of a plurality of second analysis values obtained by performing processing similar to said image analysis processing and said statistical analysis processing on said reference dynamic images of said plurality of past target objects.

9. The image processing apparatus according to claim 1, wherein
said target region includes a lung field region.

10. The image processing apparatus according to claim 1, wherein
said generation instruction information is at least one of a diagnostic region, image analysis information, statistical analysis information, and parameter information.

11. A computer-readable non-transitory storage medium storing a program executed by a computer included in an image processing apparatus according to claim 1.

12. The image processing apparatus according to claim 1, wherein
said reference statistical value includes a statistical value obtained using, as a population parameter, a photographing target parameter indicating information specific to said plurality of target objects.

13. The image processing apparatus according to claim 12, wherein the photographing target parameter is classified into at least one of sex, age, a body type and a body thickness.

14. The image processing apparatus according to claim 1, wherein
said reference statistical value includes a statistical value obtained using, as a population parameter, a disease information parameter indicating presence or absence of a disease and a state of the disease of said plurality of target objects.

15. The image processing apparatus according to claim 14, wherein the disease information parameter is classified into at least one of a healthy individual, a patient with a particular disease, and a severity of a disease.

16. The image processing apparatus according to claim 1, wherein
said reference statistical value includes a statistical value obtained using, as a population parameter, a photographing environment parameter indicating photographing environments in which said reference dynamic images have been photographed.

17. The image processing apparatus according to claim 16, wherein the photographing environment parameter classified into at least one of tube voltage, tube current, photographing time, a radiation dose, a photographing distance, a photographing direction P-A (posteroanterior view) or A-P (anteroposterior view), a position during photography (a standing position and a lying position [a supine position, a side-lying position, and a prone position]).

18. The image processing apparatus according to claim 1, wherein said reference statistical value is a range or includes a standard deviation.

* * * * *